US006697783B1

(12) United States Patent
Brinkman et al.

(10) Patent No.: US 6,697,783 B1
(45) Date of Patent: Feb. 24, 2004

(54) COMPUTER IMPLEMENTED MEDICAL INTEGRATED DECISION SUPPORT SYSTEM

(75) Inventors: Thomas Brinkman, Sparta, NJ (US); Wayne Gattinella, Greenwich, CT (US); William Kleinfelter, Ivyland, PA (US); Glen Stettin, Upper Saddler River, NJ (US); David Angaran, Powell, OH (US); J. Russel Teagarden, Brookfield, CT (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 0 days.

(21) Appl. No.: 09/161,960

(22) Filed: Sep. 29, 1998

(Under 37 CFR 1.47)

Related U.S. Application Data

(60) Provisional application No. 60/060,554, filed on Sep. 30, 1997.

(51) Int. Cl.[7] ............................................... G06F 17/60
(52) U.S. Cl. ......................................................... 705/3
(58) Field of Search .......................................... 705/2, 3

(56) References Cited

U.S. PATENT DOCUMENTS

| | | | | |
|---|---|---|---|---|
| 4,835,372 A | * | 5/1989 | Gombrich et al. | 235/375 |
| 5,153,827 A | * | 10/1992 | Coutre et al. | 604/111 |
| 5,517,405 A | * | 5/1996 | McAndrew et al. | 364/401 |

(List continued on next page.)

FOREIGN PATENT DOCUMENTS

| | | | | |
|---|---|---|---|---|
| JP | 406119360 A | * | 4/1994 | G06F/15/21 |

OTHER PUBLICATIONS

Moench, Liz, "Demand Management: The New Business in Patient Communications." Medical Marketing & Media, vol. 32, No. 1, pp. 52–62, Jan. 1997.*

Donnelly, Kathleen. "Counseling Nurses are Health Care Innovation." Pittsburgh Post–Gazette (Science, Technology & Medicine Section), p. A–9, Mar. 25, 1996.*

"The Roles of Health Management in Medicare Managed Care," Managed Care Week, vol. 6, No. 43, p. N/A, Nov. 25, 1996.*

"Merck–Medco Alliance Links Demand and Disease Management," PharmacoEconomics & Outcomes News, Nov. 1997.*

(List continued on next page.)

*Primary Examiner*—Susanna Meinecke-Díaz
(74) *Attorney, Agent, or Firm*—Irah H. Donner; Hale and Dorr LLP

(57) ABSTRACT

A software-based, integrated member decision support system provides a method for corporations, insurance carriers, health maintenance organizations, physicians, physician groups, or other clients to efficiently provide medical, pharmaceutical, and health benefit advice and information for an enrolled population. The system contains one or more databases which include member profiles, clinical information and guidelines, pharmaceutical information and guidelines, health benefit information, and optional additional information. A caller establishes communication with the system, which directs the caller to an operator who provides the caller with medical, pharmaceutical, and/or health benefit advice based on an inquiry from the caller and the information stored on the system. The system may automatically alert the caller or the operator of important medical or pharmaceutical information. At the conclusion of the call, the system or the system with the operator's input, may update the caller's member profile, request written materials, generate referrals, order prescriptions, or generate reports.

17 Claims, 25 Drawing Sheets

U.S. PATENT DOCUMENTS

| | | | | |
|---|---|---|---|---|
| 5,583,758 A | * | 12/1996 | McIlroy et al. | 395/202 |
| 5,594,638 A | * | 1/1997 | Iliff | 395/203 |
| 5,758,095 A | * | 5/1998 | Albaum et al. | 705/2 |
| 5,764,923 A | * | 6/1998 | Tallman et al. | 705/3 |
| 5,845,253 A | * | 12/1998 | Rensimer et al. | 705/2 |
| 5,845,255 A | * | 12/1998 | Mayaud | 705/3 |
| 5,884,273 A | * | 3/1999 | Sattizahn et al. | 705/3 |
| 5,953,704 A | * | 9/1999 | McIlroy et al. | 705/2 |
| 5,991,729 A | * | 11/1999 | Barry et al. | 705/3 |
| 6,012,034 A | * | 1/2000 | Hamparian et al. | 705/2 |
| 6,014,631 A | * | 1/2000 | Teagarden et al. | 705/3 |
| 6,029,138 A | * | 2/2000 | Khorasani et al. | 705/2 |
| 6,067,523 A | * | 5/2000 | Bair et al. | 705/3 |
| 6,081,786 A | * | 6/2000 | Barry et al. | 705/3 |

OTHER PUBLICATIONS

"Merck–Medco Introduces Well Informed™ Consumer Services," Retreived from Internet <URL: http://www.merck–medco.com/medco> on May 2, 2000, Sep. 1997.*

Barmash, Isadore, "Walgreen Didn't Know It Had a Friend at the FTC," The Emporium, Jun. 1996.*

Slezak, Michael, "Mail–Order Changes Its Colors," American Druggist, vol. 212, No. 8, pp. 22(5), Dec. 1995.*

* cited by examiner

COMPUTER IMPLEMENTED MEDICAL INTEGRATED DECISION SUPPORT SYSTEM

This application is a continuation of provisional U.S. patent application No. 60/060,554, filed Sep. 30, 1997, incorporated herein by reference.

BACKGROUND OF THE INVENTION

1. Field of the Invention

The present invention generally relates to a. computer implemented and/or assisted health information system for tracking and/or ensuring appropriate patient care, whereby the system facilitates client access to health professionals for confidential health advice, personalized treatment advice, personalized pharmaceutical advice and service, and personalized health benefit and account information.

2. Background of the Related Art

Health care costs currently represent a significant portion of the United States Gross National Product, and continue to rise at an exceptional pace. A significant portion of these increased costs represents the health care providers' inability to efficiently compile and communicate health benefit and account referral information, provide guidance on prescription drug use, and administer confidential health advice relating to items such as treatment options and disease management. Accordingly, many patients are deprived of access to the most needed medical care and information, and many patients who do receive medical care and information often do not receive information tailored to patient-specific needs in an expedient and efficient manner.

We have determined that if a system were available which allowed callers to obtain patient specific medical advice, pharmaceutical instructions and guidance, referrals, and benefits information through a single point of access, callers could quickly obtain relevant information to address their questions, concerns or problems. System users/clients could also control medical costs by efficiently identifying courses of medical and pharmaceutical treatment that may benefit the patient, by providing ready access to medical and pharmaceutical guidelines, by providing efficient access to benefit and referral information, and by integrating these elements into a single administrative function so that system administration is streamlined and a single means of tracking and/or monitoring usage is available.

One prior attempt to address the health care problem is called Ask-A-Nurse, wherein trained nurses provide health care information by telephone around-the-clock. A person with a medical problem calls an 800 number and describes the problem to the nurse. The nurse uses a computer for general or diagnostic information on the ailment or complaint mentioned by the caller. The nurse may then refer the caller to a doctor from a computerized referral list for a contracting hospital or group of hospitals. A managed care option called Personal Health Advisor is similar and adds the capability for the caller to hear pre-recorded messages on health topics 24 hours a day.

Another prior health system provides a computerized service that answers health care questions and advises people in their homes. A Health Maintenance Organization ("HMO") may provide this service to its members in a particular geographic area. To get advice at home, an HMO member connects a box device to a telephone and calls a toll-free 800 number. Using a keyboard that is part of the box, the user answers questions displayed on a screen of the box relating to the user's symptoms. Depending on the answers, the user might be told to try a home remedy, be called by a nurse or doctor, or be given an appointment to be examined.

Several problems exist with these prior medical advice systems. First, the Ask-A-Nurse and Personal Health Advisor systems have high costs associated with having a nurse answer each telephone call. Second, these systems fail to include any means of providing callers with referrals, prescription refills, or medical benefit information in conjunction with the medical advice. Third, and significantly, these systems provide no means of either providing information that is tailored to a patient's specific needs based on the patient's medical history or updating the patient's records based on the information provided.

Prior methods of administering confidential health advice include U.S. Pat. No. 5,660,176 to Iliff, incorporated herein by reference. Iliff is directed to a computerized medical diagnostic and treatment advice system. Referring to FIG. 1, the components of the computerized medical diagnostic and treatment advice system 100 are shown. A personal computer 102 includes a plurality of components within an enclosure 104. A plurality of telephone lines 106 interface the public telephone network 108 to the computer 102. One of telephone lines 106 is shown to be switched via network 108 to connect with a telephone 110 that is used by a person desiring medical advice (user) 112.

FIG. 2 is a block diagram illustrating a conceptual view of the database files and processes of the system of FIG. 1. If the caller is the patient, a patient registration process 252 is used to register new or first-time callers. If the caller is not the patient, an assistant registration process 274 is used to register new or first-time assistants. An assisted registration process 278 is also available. A patient login process 250 and an assistant login process 272 are used to identify a patient or assistant who has previously registered into the system. An assisted login process 276 is also available.

The master patient and assistant enrollment database 260 is created at run-time by one of the registration processes 252, 274, or 278. This database 260 is read by the patient login process 250 or the assisted patient login process 276 to validate a patient's identity at login time, and by the assistant login process 272 to validate an assistant's identity at login time. The database 260 is essentially a master file of all registered patients and assistants indexed by their patient ID number or assistant ID number, respectively.

In Iliff, the medical diagnostic and treatment advice is provided to the general public over a telephone network. The system uses a new authoring language, interactive voice response and speech recognition technology, to enable expert and general practitioner knowledge to be encoded for access by the public. However, the system in Iliff is designed to respond to caller complaints with standard information, and provides no process for ensuring and/or designing patient-specific care, as it does not use patient history (such as known conditions or previous advice given) when providing medical advice. Further, it only responds to caller inquiries and provides no means of alerting the caller of important items, such as prescription drug refill reminders, which may not have been the subject of the caller's inquiry. In addition, the system provides only medical advice, and includes no means for responding to callers' pharmaceutical or health benefit inquiries.

U.S. Pat. No. 5,471,382, to Tallman et al., incorporated herein by reference, relates to a medical network management system comprising a data processing system, which includes memory that contains a patient assessment stored program and a patient database, a display, and an input means. The patient assessment stored program includes means for checking patient eligibility, means for selecting a branched chain logic algorithm for assessing a patient for an appropriate timing and type of medical care, and branched chain logic algorithms to assess the patient for an appropriate timing and level of medical care. The system in Tallman et al. includes a member assessment component wherein the patient's risk is assessed, and a provider information component wherein the system helps the patient identify an appropriate doctor, clinic, hospital, or other provider to meet their needs. Accordingly, the system in Tallman et al. assists patients in obtaining an appropriate level of care from an appropriate provider. However, the system in Tallman is not designed to provide actual health counseling or disease management services. Further, the system in Tallman et al. does not provide the patient with prerecorded messages of health information, pharmaceutical advice and service, or health benefit information.

At the other end of the spectrum, prior methods for providing pharmaceutical advice include reference books and charts that correlate known uses of prescription drugs with medical conditions. FIGS. 3a–3b identify the methods by which this correlation may occur. FIG. 3a indicates that the method may identify a drug and list the conditions for which the drug is known to be effective. In the alternative, FIG. 3b indicates that the method may list medical conditions and identify the drugs which are known to be effective to treat each condition.

These prior methods of correlating prescription drugs and medical conditions also present several problems. First, the methods are reactive to user inputs and do not proactively alert the user of the suitability or unsuitability of particular drugs for particular conditions. Further, none of the previous systems automatically alert the user of items such as possible side effects, drug interaction effects, prescription refill reminders, or prescription renewal reminders.

U.S. Pat. No. 5,758,095 to Albaum et al., incorporated herein by reference, represents a computer-assisted method of providing pharmaceutical advice. Albaum et al. describes a system and method for ordering and prescribing drugs for a patient. The system in Albaum et al. also allows the user, typically a pharmacist, to access a database which includes current and previously-prescribed medications for individual patients. The system also contains a database of prescription drug information to help the pharmacist identify possible reactions to particular drugs.

The prior art methods such as that in Albaum et al. contain several disadvantages. First, the methods provide no means for a caller to remotely access the system and thus provide no means for a patient to obtain prerecorded health information. Further, the systems are limited to the ordering of prescription drugs and provide no means for identifying or selecting appropriate drugs or responding to patients' medical inquiries.

Accordingly, we have determined that it is desirable to provide a method and/or system that allows clients to provide confidential health advice and disease management advice that is directly tailored to member-specific needs.

We have also determined that it is desirable to provide a method and/or system that allows members to obtain pre-recorded health-related messages at all times.

We have also determined that it is desirable to provide a method and/or system that allows members to obtain confidential pharmaceutical guidance, reminder, and alert information.

We have also determined that it is desirable to provide a method and/or system that allows the client to update member history files to include information based on the member's call.

We have also determined that it is desirable to provide a method and/or system to provide a single, integrated means of tracking and/or monitoring client and member usage of health, pharmaceutical, and benefit account management services.

SUMMARY OF THE INVENTION

It is therefore a feature and advantage of the present invention to provide confidential health advice and disease management advice that is directly tailored to member-specific needs.

It is another feature and advantage of the present invention to provide members a means to obtain prerecorded health-related messages at all times.

It is another feature and advantage of the present invention to allow members to obtain confidential pharmaceutical guidance, reminder, and alert information.

It is another feature and advantage of the present invention to provide a method and/or system that allows the client to update member history information during and after each member call.

It is yet another feature and advantage of the present invention to provide a single, integrated means of tracking and/or monitoring client and member usage of health, pharmaceutical and account management services.

The above and other features and advantages are achieved through the use of a novel health management system as herein disclosed. In accordance with the preferred embodiment of the present invention, a computer system contains one or more databases which include member profiles, clinical information and guidelines, pharmaceutical information and guidelines, health benefit information, and optional additional information. A caller establishes communication with the system, which automatically directs the caller to an operator who provides the caller with medical, pharmaceutical, and/or health benefit advice based on an inquiry from the caller and the information stored on the system. The system may automatically alert the caller or the operator of important medical or pharmaceutical information. During the call and at the conclusion of the call, the system, or the system with the operator's input, may update the caller's member profile, request written materials, generate referrals, order prescriptions, and/or generate reports.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

The scope of the invention, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter which illustrate preferred embodiments of the invention.

BRIEF DESCRIPTION OF THE DRAWINGS

FIGS. 15a–15b illustrate examples of member profile information screens;

FIG. 19 illustrates an example screen by which an operator may enter symptoms that are described by a caller;

NOTATIONS AND NOMENCLATURE

Figure 1:
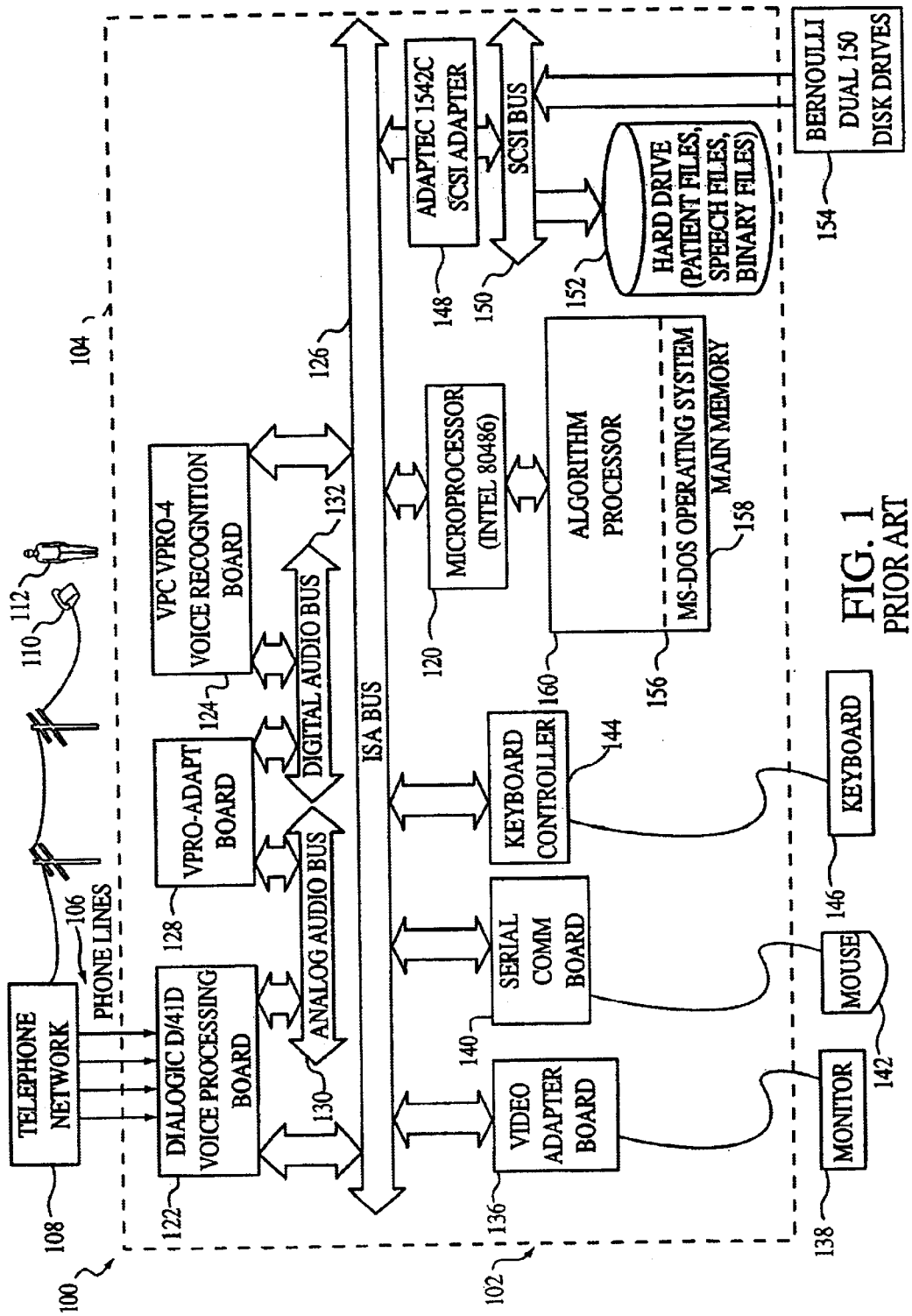
FIGS. 1, 2, 3a, and 3b depict prior art.
Figure 2:
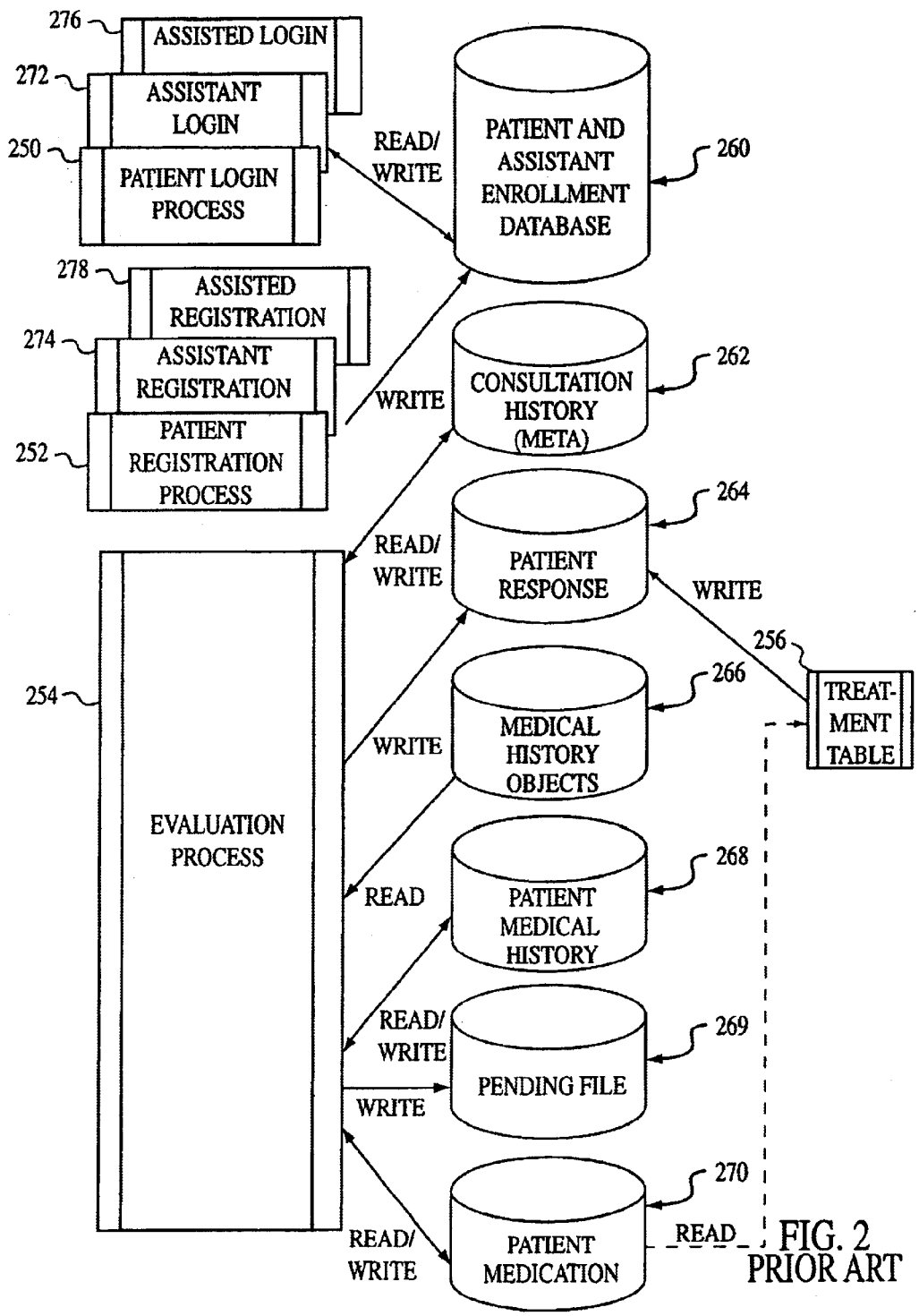
Figure 3A:
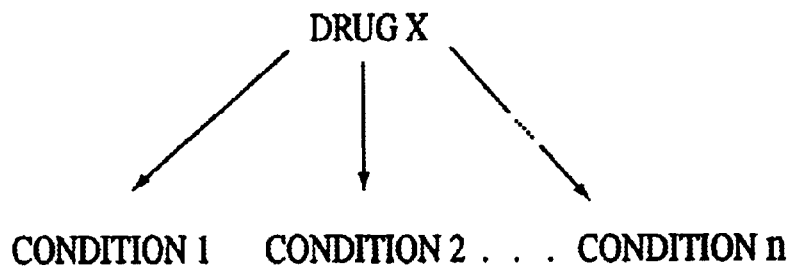
Figure 3B:
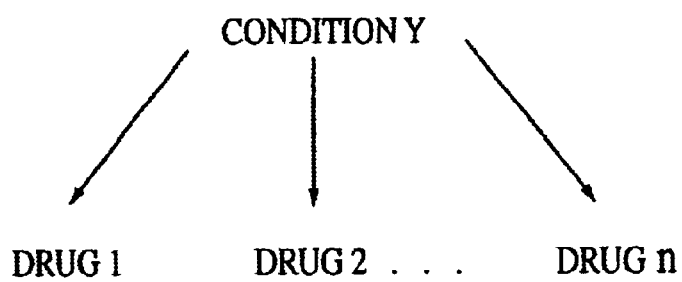
Figure 4:
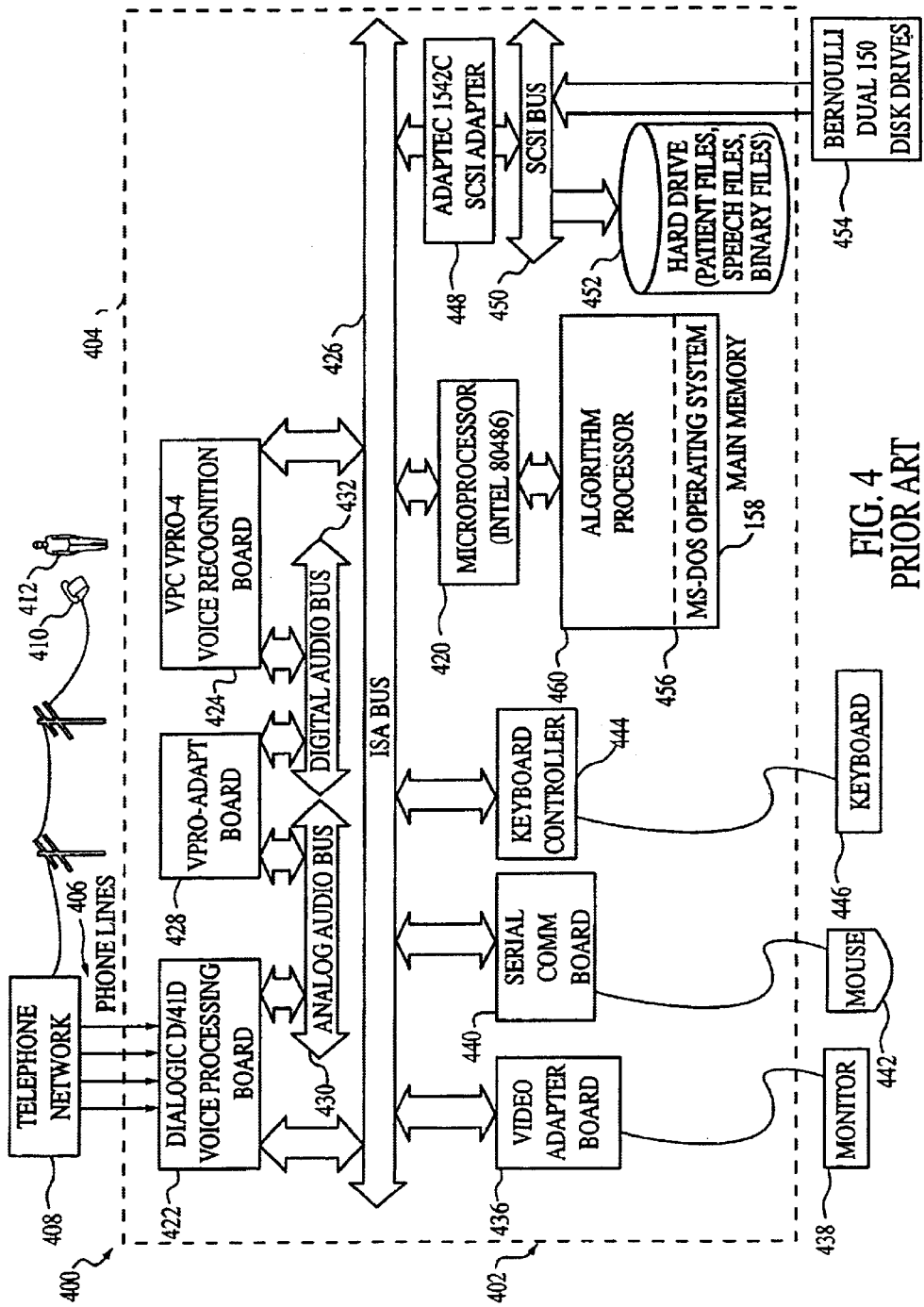
FIG. 4 is a block diagram illustrating the components of a central computer system, which is used in a preferred embodiment of the present invention.

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. While the present invention contemplates the use of an operator to access the invention, a human operator is not necessary, or desirable in most cases, to perform the actual functions described herein which form part of the present invention; the operations are machine operations. Useful machines for performing the operation of the present invention include general purpose digital computers or similar devices.

The present invention also relates to an apparatus for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct a more specialized apparatus to perform the required method steps. The required structure for a variety of these machines will appear from the description given.

DESCRIPTION OF THE PREFERRED EMBODIMENT OF THE INVENTION

I. Introduction

The integrated member decision support system is a computer assisted and/or implemented system designed to gather, maintain and update the medical, pharmaceutical, demographic, psychographic, and health benefit information of members; maintain and provide medical, pharmaceutical, and/or customer service information and advice; and generate and deliver data and reports.

The present invention improves or maintains the quality of member care while controlling or reducing health care costs. The system achieves this goal by collecting, storing, and processing extensive information relating to member histories, health care and prescription drug benefit plans, and clinical and pharmaceutical information and guidelines. The system provides the client with an efficient means to access such information and identify the information that is relevant and appropriate to member-specific needs.

For the purposes of the present invention, a "client" is broadly defined to include an HMO, self-insured employer group, third-party administrator, physician group, physician network, pharmacy group, pharmacy network, or other health care program analyst or insurance carrier. An "operator" is broadly defined to include any person who uses the present invention on behalf of the client, and may include a nurse, a pharmacist, a customer service representative, a clerk, a telephone operator, or any other person.

II. System Overview

Figure 5:
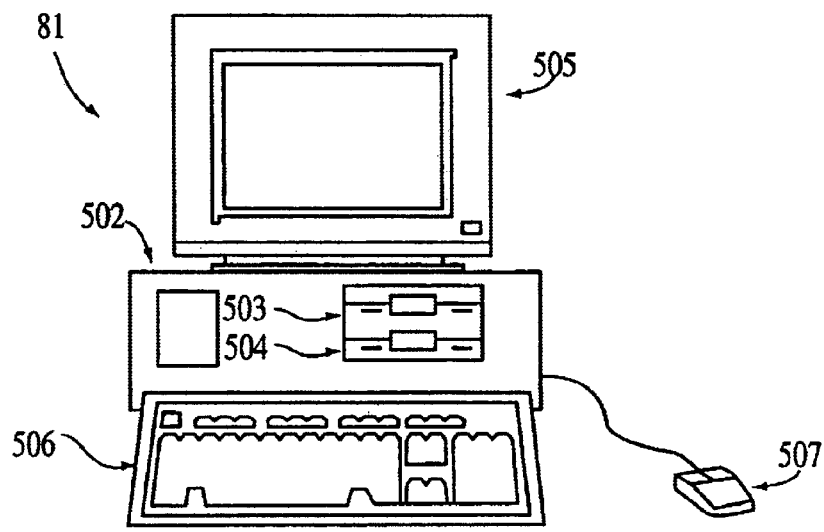
FIGS. 5 and 6 illustrate a computer of a type suitable for implementing and/or assisting in the implementation of the processes described herein.

The present invention requires a network of serving computers, one or more client computers, and a means for communicating between the central computer and the client. FIG. 5 illustrates a computer of a type suitable for carrying out the invention. Viewed externally in FIG. 5, a computer system designated by reference numeral 501 has a central processing unit 502 having disk drives 503 and 504. Disk drive indications 503 and 504 are merely symbolic of a number of disk drives which might be accommodated by the computer system. Typically these would include a floppy disk drive such as 503, a hard disk drive (not shown externally) and a CD ROM or digital video disk indicated by slot 504. The number and type of drives varies, typically with different computer configurations. Disk drives 503 and 504 are in fact options, and for space considerations, may be omitted from the computer system used in conjunction with the processes described herein.

The computer also has a display 505 upon which information is displayed. The display is optional for the network of computers used in conjunction with the system described herein. A keyboard 506 and a pointing device 507 such as mouse will be provided as input devices to interface with the central processing unit 502. To increase input efficiency, the keyboard 506 may be supplemented or replaced with a scanner, card reader, or other data input device. The pointing device 507 may be a mouse, touch pad control device, track ball device, or any other type of pointing device.

Figure 6:
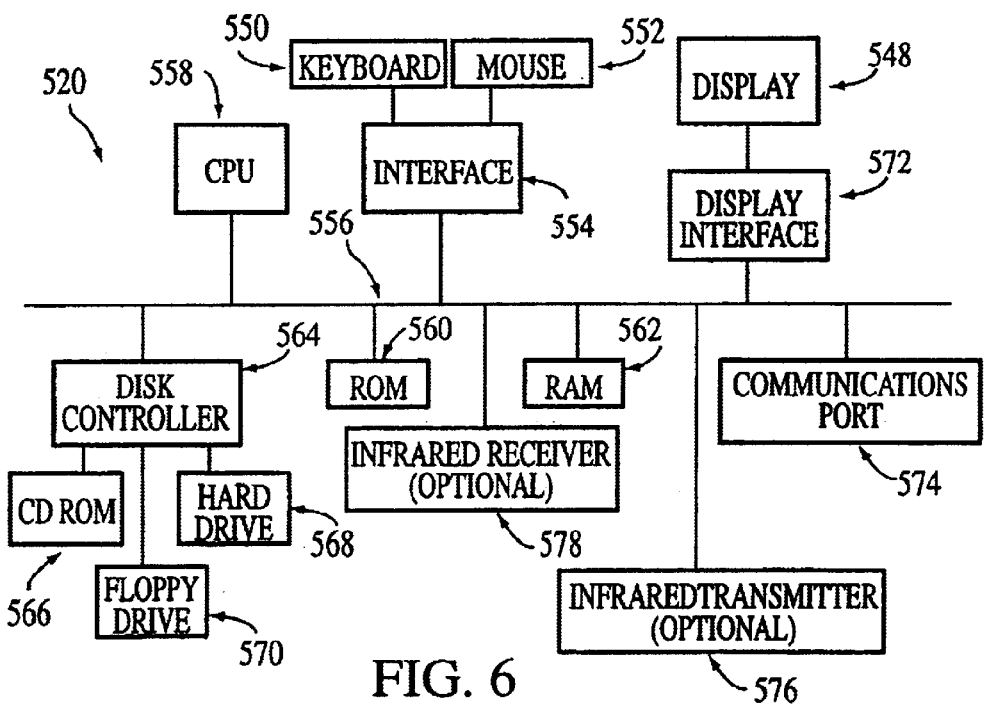

FIG. 6 illustrates a block diagram of the internal hardware of the computer of FIG. 5. A bus 556 serves as the main information highway interconnecting the other components of the computer. CPU 558 is the central processing unit of the system, performing calculations and logic operations required to execute a program. Read only memory (ROM) 560 and random access memory (RAM) 562 constitute the main memory of the computer.

A disk controller 564 interfaces one or more disk drives to the system bus 556. These disk drives may be floppy disk drives such as 570, or CD ROM or DVD (digital video disk) drives such as 566, or internal or external hard drives 568. As indicated previously, these various disk drives and disk controllers are optional devices.

A display interface 572 permits information from the bus 556 to be displayed on the display 548. Again as indicated, display 548 is also an optional accessory for the network of computers. Communication with external devices occurs utilizing communication port 574.

In addition to the standard components of the computer, the computer also includes an interface 554 which allows for data input through the keyboard 550 or pointing device such as a mouse 552.

Figure 7:
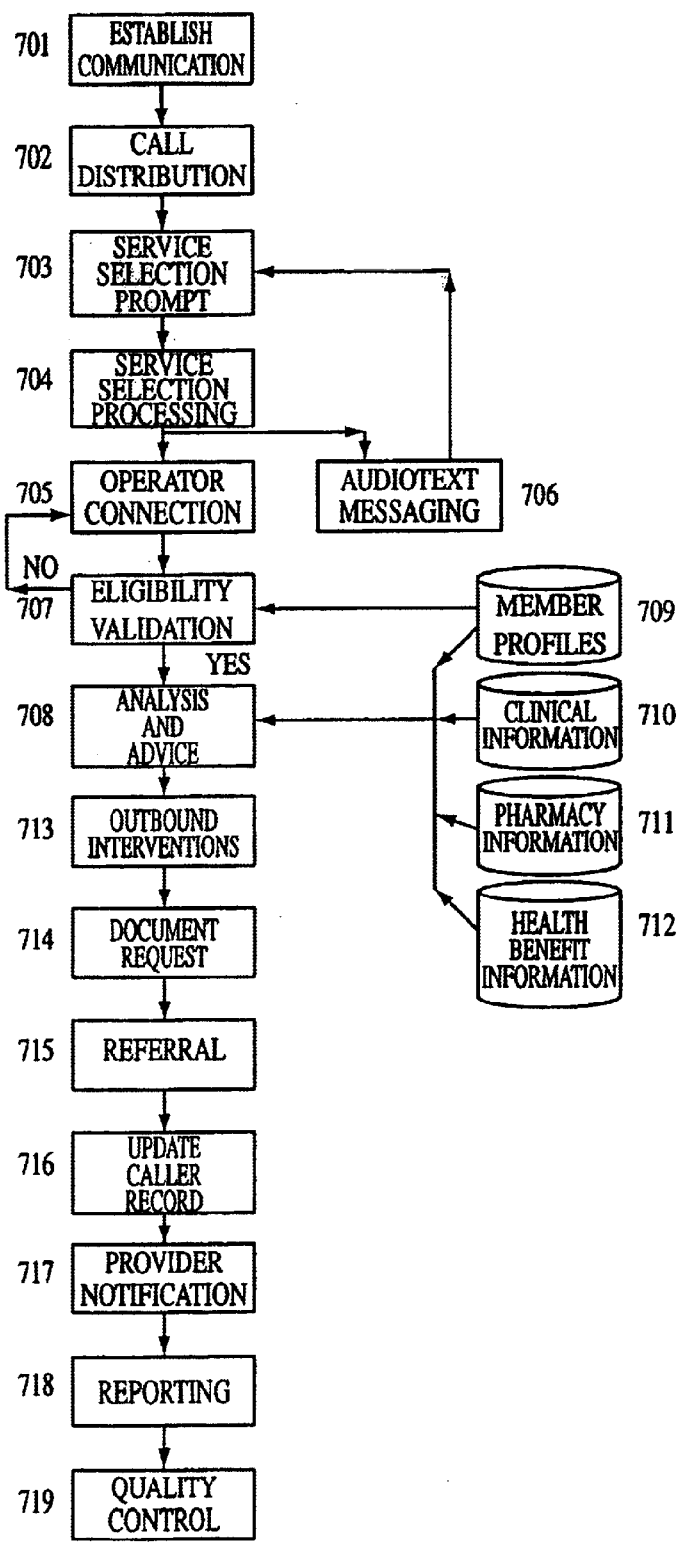
FIG. 7 is a block diagram of the primary components of the system process.

FIG. 7 illustrates a block diagram of the primary components of the health management system process. The caller, which is typically a member of a health plan but which may also be a member representative, health care provider, health care administrative personnel, or other person, establishes communication 701 with the system or the client. The method of access is preferably a telephone voice line, in which case the caller calls the client, who accesses the system via a client computer, or a central operator, who accesses the system via the network of computers. The caller may optionally use other means of access such as e-mail, the Internet, or a direct computer connection to directly access the system. When the method of access is a telephone line, the system may use multiple telephone lines in order to provide the system or the client with preliminary identification information about the caller and/or the caller's request. For example, members affiliated with one client may be directed to use one primary telephone number to access the system, while members affiliated with another client may be provided a different access number. The communication method may establish the communication directly between the caller and a central system operator, or it may establish communication between the caller and the client. Members may also be provided with separate telephone numbers for separate types of service. For example, callers may dial one number to obtain pharmaceutical information, a different number for health or disease management counseling, and a third number for customer service information. An automated call distributor 702 routes the call to the client, the central system operator, or to a specific client operator based on the telephone number the caller uses to access the system.

The system, and preferably the automated call distributor portion of the system, then prompts the caller to select a service. Preferably, the service selection prompt 703 is a prerecorded message that directs the caller to select a service from a menu of options. For example, the system may prompt the caller to select one number for clinical assistance, another number for prescription refills, a third number for account or billing information, a fourth number for referrals, etc. The prompt may also be layered, for example with one or more additional levels of prerecorded messages when the caller enters a response to a prompt. optionally, in lieu of or in addition to the prerecorded message, the system may connect the caller with a human operator who accesses the system and enters the service selection into the system on behalf of the caller. In such a case, the system provides the operator with prompts to guide the caller's selections. For example, referring to FIG. 12, the system may prompt the operator to welcome the caller with a welcome script 1201. The operator may use a transfer prompt 1202 to transfer the caller to the appropriate service based on the caller's request. An optional "emergency" prompt 1203 may also be provided to allow the caller to bypass the automated call distributor and directly speak to a nurse or obtain standard emergency instructions (such as instructions to call a local emergency service such as the "911" service).

In response to the caller's selection, referring again to FIG. 7 the system processes 704 the caller's service selection by connecting 705 the caller to a nurse, a pharmacist, a customer service representative, or other operator depending on the caller's selection. optionally, the prompt function 703 may allow the caller to access a touch-tone menu which invites the caller to listen to prerecorded audiotext messages 706 on a variety of health care- and/or billing-related topics. The caller may request to speak with an operator for assistance with this touch-tone menu of prerecorded messages. If the caller accesses the system by computer, Internet, or another non-voice method, the prerecorded messages may be in the form of electronic document files which the caller can access and display at the caller's terminal. After a message is complete, or if the caller chooses to end a message before it is complete, the system returns the caller to the menu of prerecorded messages, or, optionally, to the service selection prompt.

Figure 12:
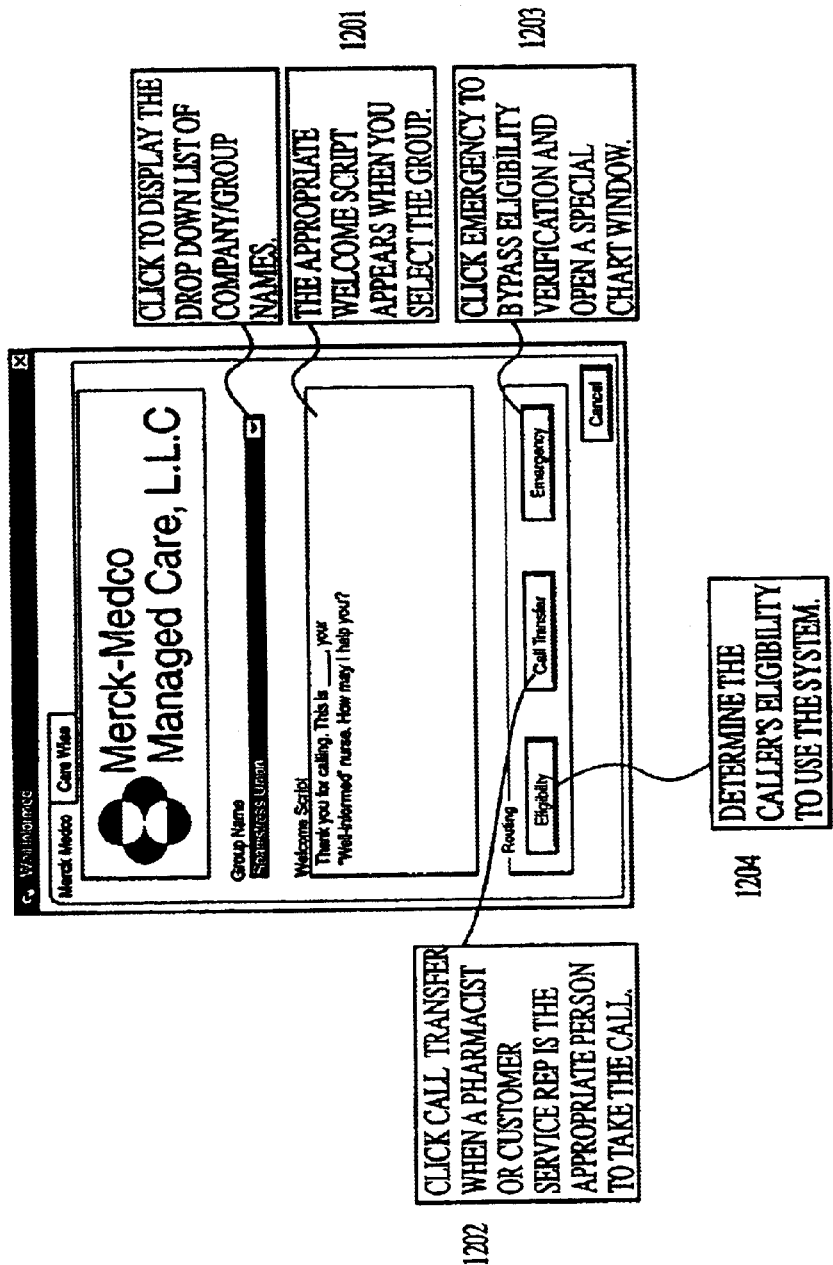
FIG. 12 illustrates an example of a welcome screen or screen portion that an operator may use in the present invention.

Preferably after the operator connection 705, or optionally before the service selection prompt 703 or service selection processing 704, the system validates 707 that the caller is eligible to use the system. The eligibility validation function 707 first prompts the caller to provide identification information. The caller may provide such information by speaking it to the operator (which may be a nurse, pharmacist, customer service representative, or other person) who subsequently enters the information into the system via a client or central computer (an example of the eligibility prompt 1204 is illustrated in FIG. 12); by entering identification information such as an access code or account number on the telephone keypad; or, if the caller accesses the system via computer, by entering such identification information on a computer keyboard. If the identification information is an access code, the access code may consist of the caller's name, social security number, account number, member identification or other unique form of identification. The system may optionally include a voice recognition system which allows the caller to speak the access code into the telephone in lieu of entering the code via the keypad.

The system verifies the caller's eligibility by comparing the caller's identification information with information stored in a database of member profiles 709 of eligible callers. Optionally, the service may first search the database using one access code, such as a member identification number, and then subsequently by the caller's name if the access code is not found in the database. If the system verifies that the caller is eligible to access the system, the system provides the client/operator with additional information from the member profile database 709 about the caller, such as the caller's name and dependent name(s), address, city, state, zip code, telephone number, health benefit plan information, prescription drug history, self-reported health information, and recent contact history. The self-reported health information is information provided by the caller, either during the call or on a prior occasion, and may include data such as allergies, existing health conditions, and demographics. The recent contact history includes information entered by the client during previous calls by the same caller. The system provides the user with this member profile information very quickly, preferably in not more than a few seconds, more preferably in less than two seconds on average. The system displays the information on the client computer or central computer, depending on the location of the operator.

Figure 13:
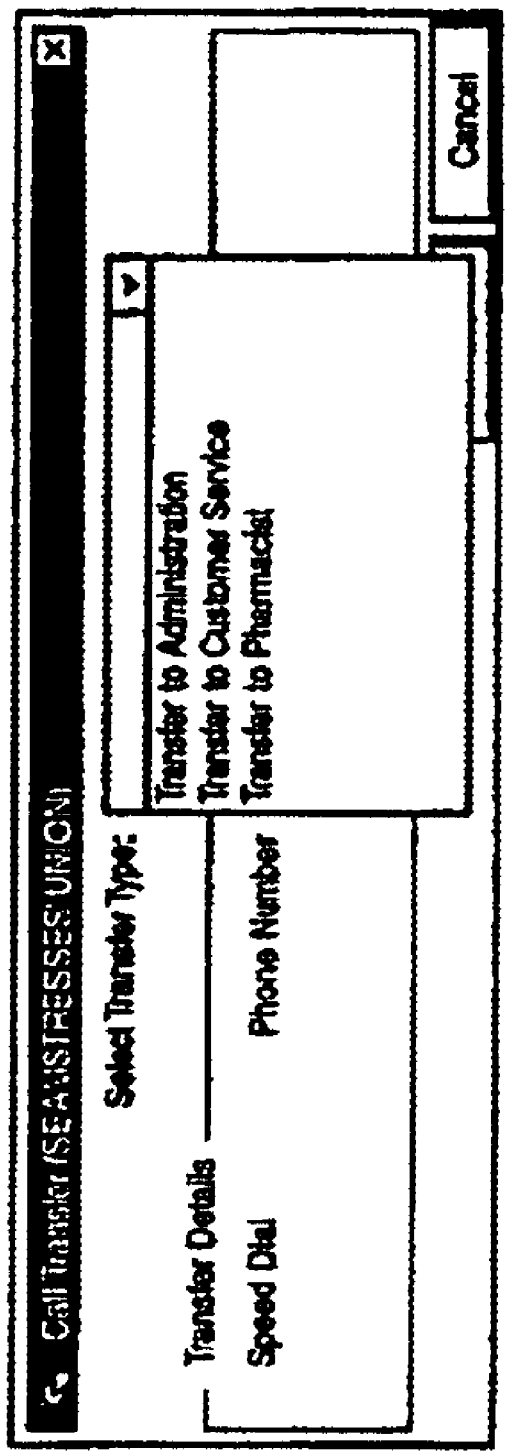
FIG. 13 illustrates an example of a screen or screen portion that an operator may use to transfer a caller to an appropriate service.
Figure 14:
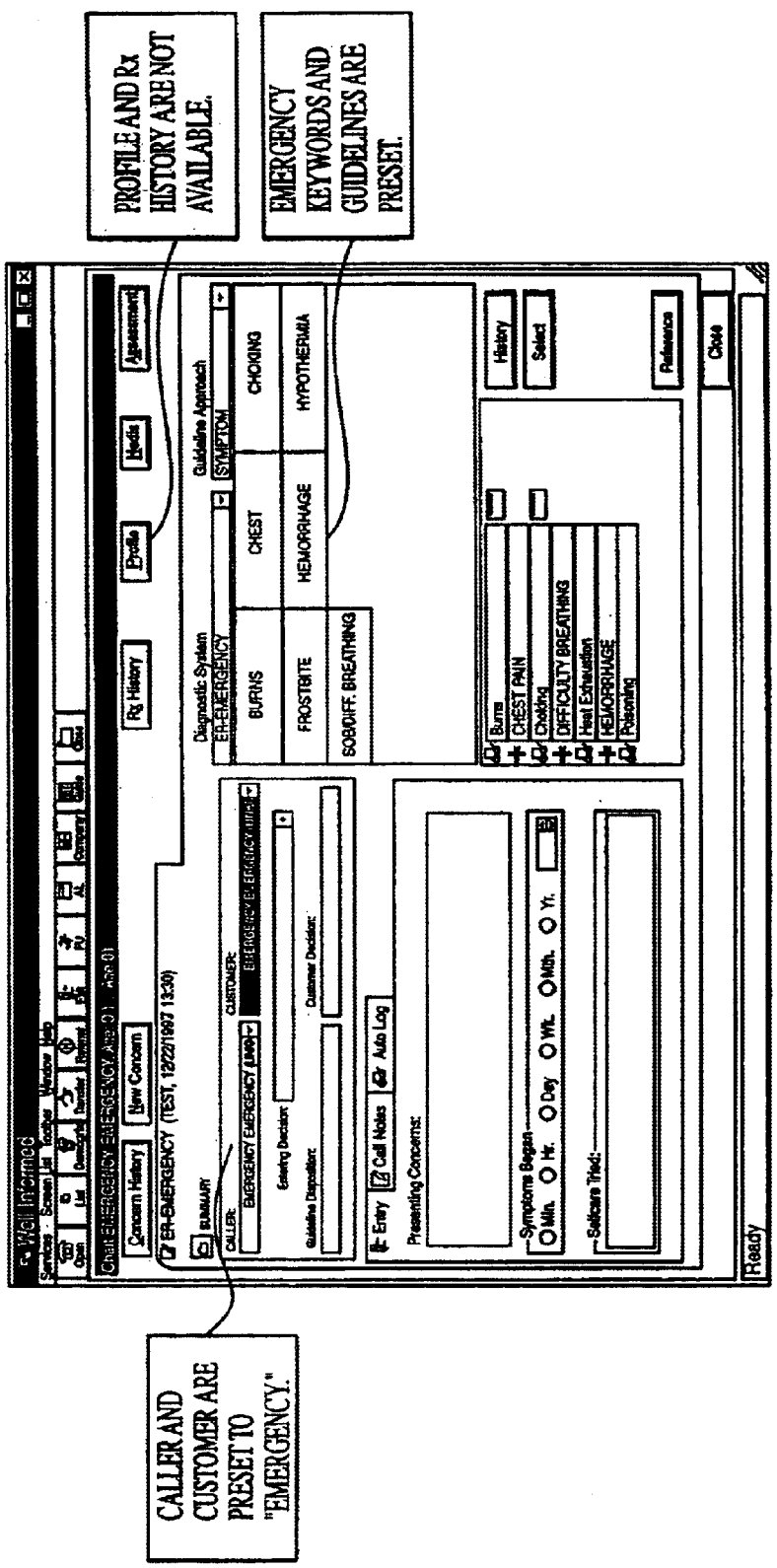
FIG. 14 illustrates an example of a screen that an operator may use if a caller has an emergency.

If the system determines that the caller is not eligible to use the system, the caller may be automatically or manually transferred to an operator 705 (which, as noted above, may be a nurse, pharmacist, customer service representative, or other person) who can further assist the caller and/or help the caller establish eligibility. For example, when an operator uses the system to assist a caller, the operator may use a call transfer screen such as that illustrated in FIG. 13, which may appear after the operator selects the transfer prompt 1202 illustrated in FIG. 12. If the caller has an emergency, the operator may optionally access the system using the emergency prompt 1203 and provide the caller with assistance as if the caller were an eligible caller, although in such circumstance the operator will not have the benefit of the caller's self-reported health information or recent contact history. An example of the emergency assistance screen that will be available to the operator appears in FIG. 14.

Figure 15A:
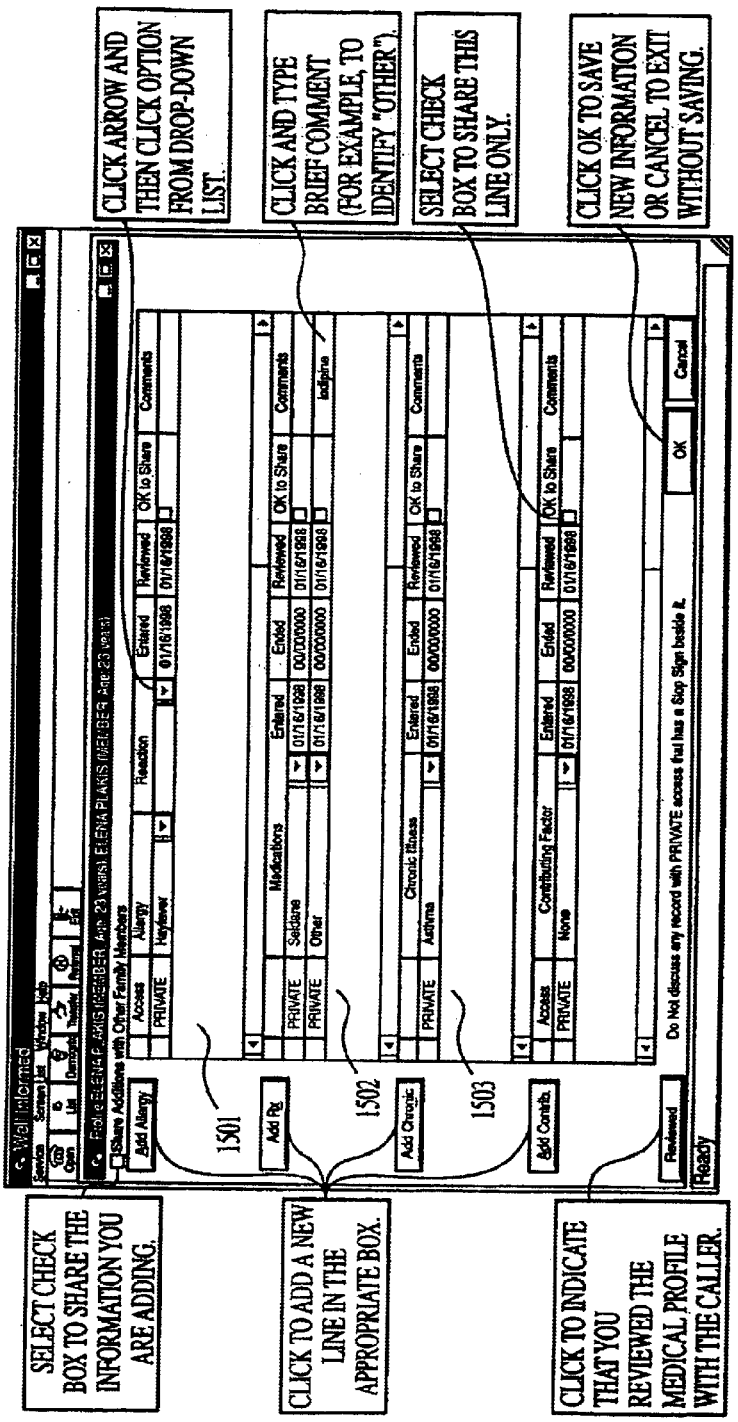
Figure 15B:
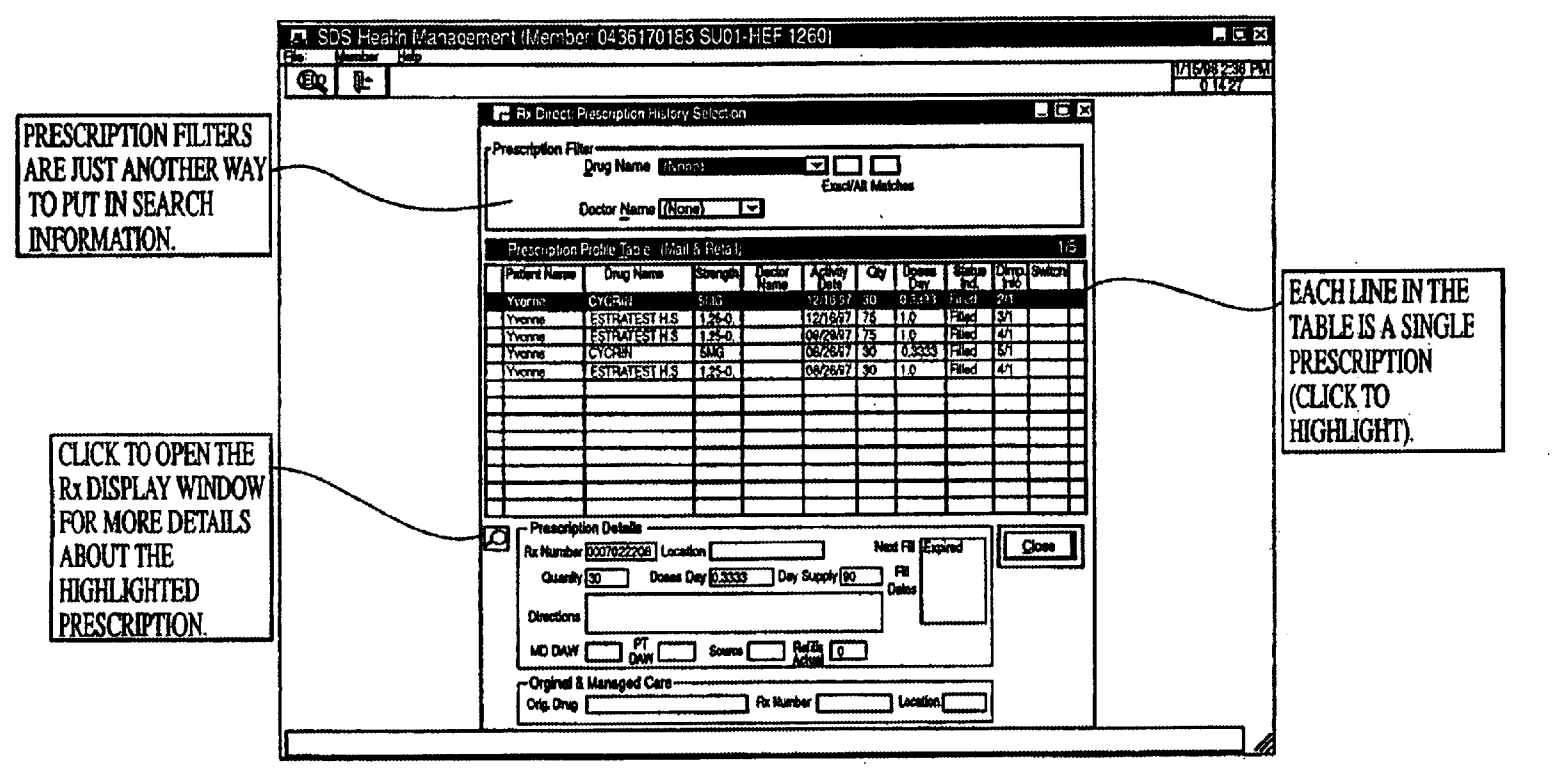

Referring again to FIG. 7, after the system validates the caller's eligibility, the caller explains the reason for the call and the operator (who, at this point, is typically a nurse, but who may also be a pharmacist, customer service representative, or other person, depending on the nature for the call) uses the network of computers or client computer to access information stored on the system to provide analysis and advice 708, or to transfer the caller to an appropriate operator, in response to the caller's inquiry. As noted above, the system provides the operator with member profile information 709 such as the caller's health benefit plan. information, prescription drug history, self-reported health information, and recent contact history. For example, referring to FIG. 15a, a member's profile may include areas that lists the member's allergies 1501, prescriptions 1502, and pre-existing health conditions 1503. FIG. 15b illustrates another example of how the system may display a member's prescription history to an operator.

Referring again to FIG. 7, the system also provides the operator the ability to access databases that store clinical information 710 such as clinical guidelines, rules, algorithms, operating protocols, and/or procedures to help the operator identify recommended forms of treatment, medications, or courses of action, and to thus counsel the caller accordingly; pharmaceutical information 711 such as prescription drug side effects and complications that may be associated with particular drugs or combinations of drugs; and health benefit information 712 such as insurance company rules, member information, and benefit plan resources. The clinical guidelines may cover a multitude of medical symptoms, conditions, procedures and topics, and they may include general information about effective and appropriate prescription and over-the-counter medications. Optionally, the system may restrict the operator's ability to access certain databases or portions thereof based on the operator's level of authorization.

Figure 16:
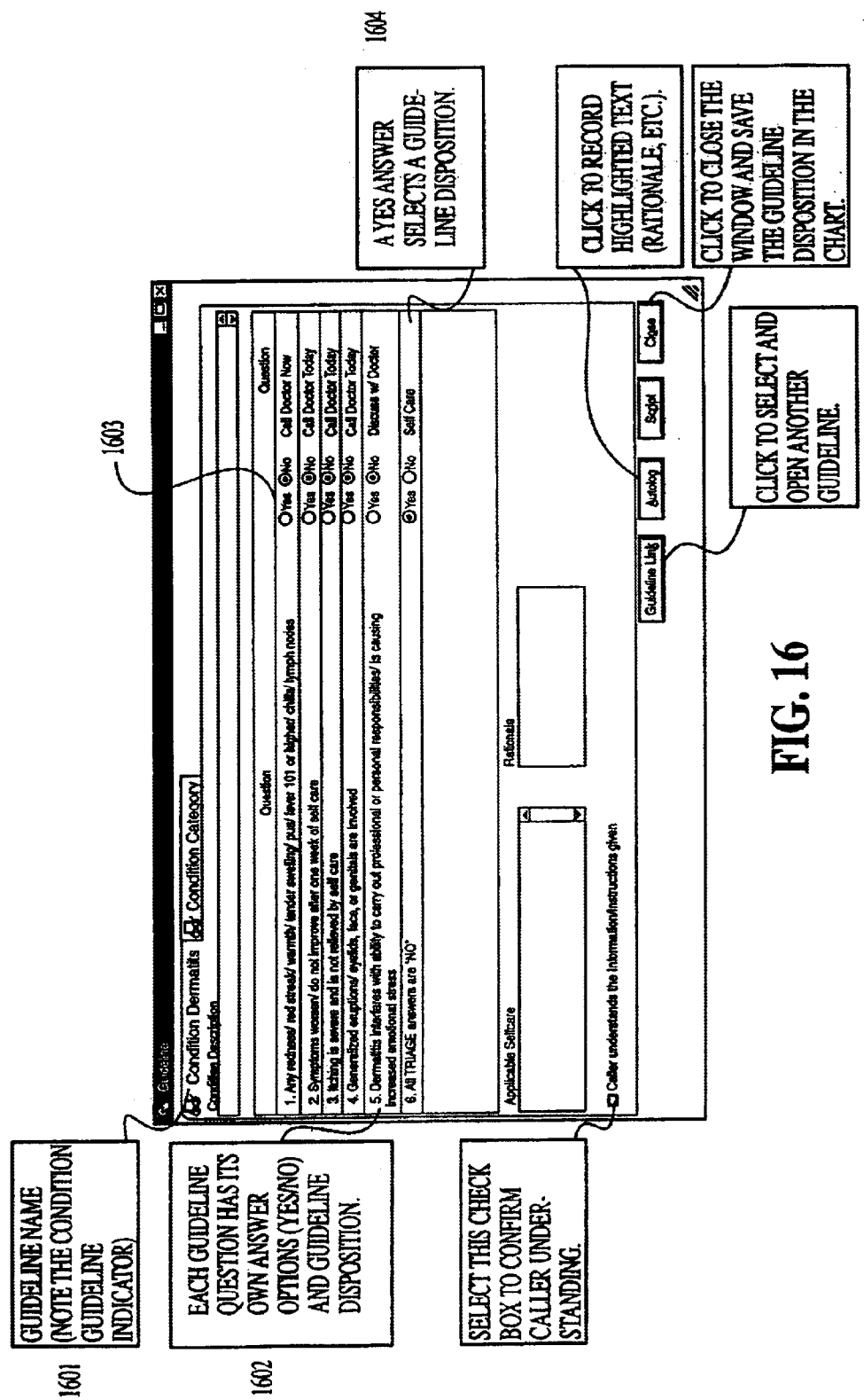
FIG. 16 illustrates, by way of an example screen, the process by which the present invention may guide an operator to obtain information and provide advice.
Figure 17A:
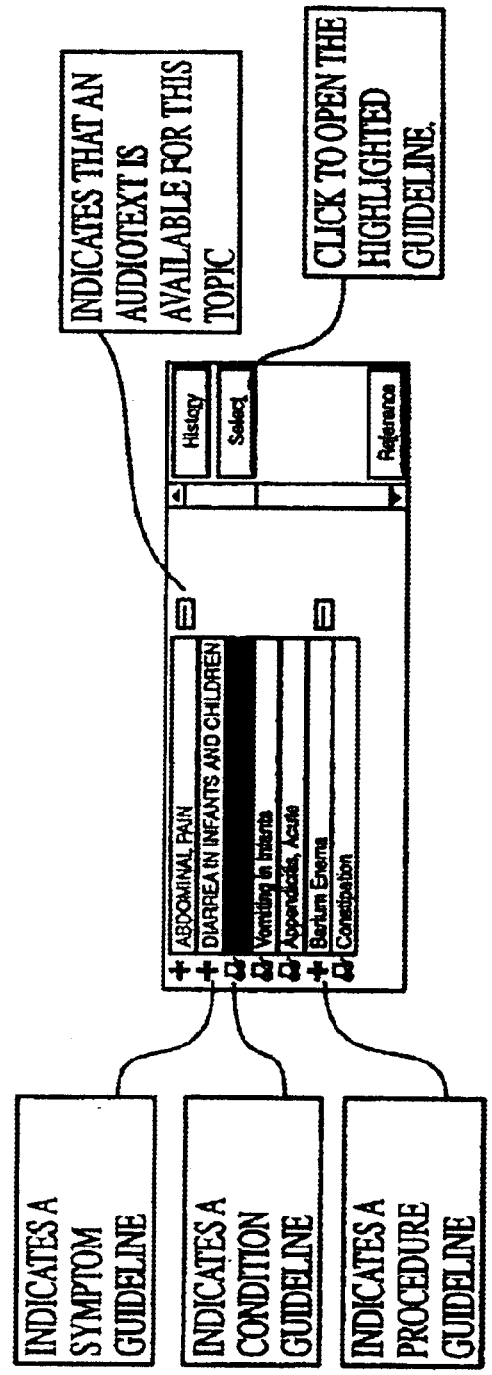
FIGS. 17a and 17b illustrate examples of the screens or screen portions from which an operator may select one or more guidelines.
Figure 17B:
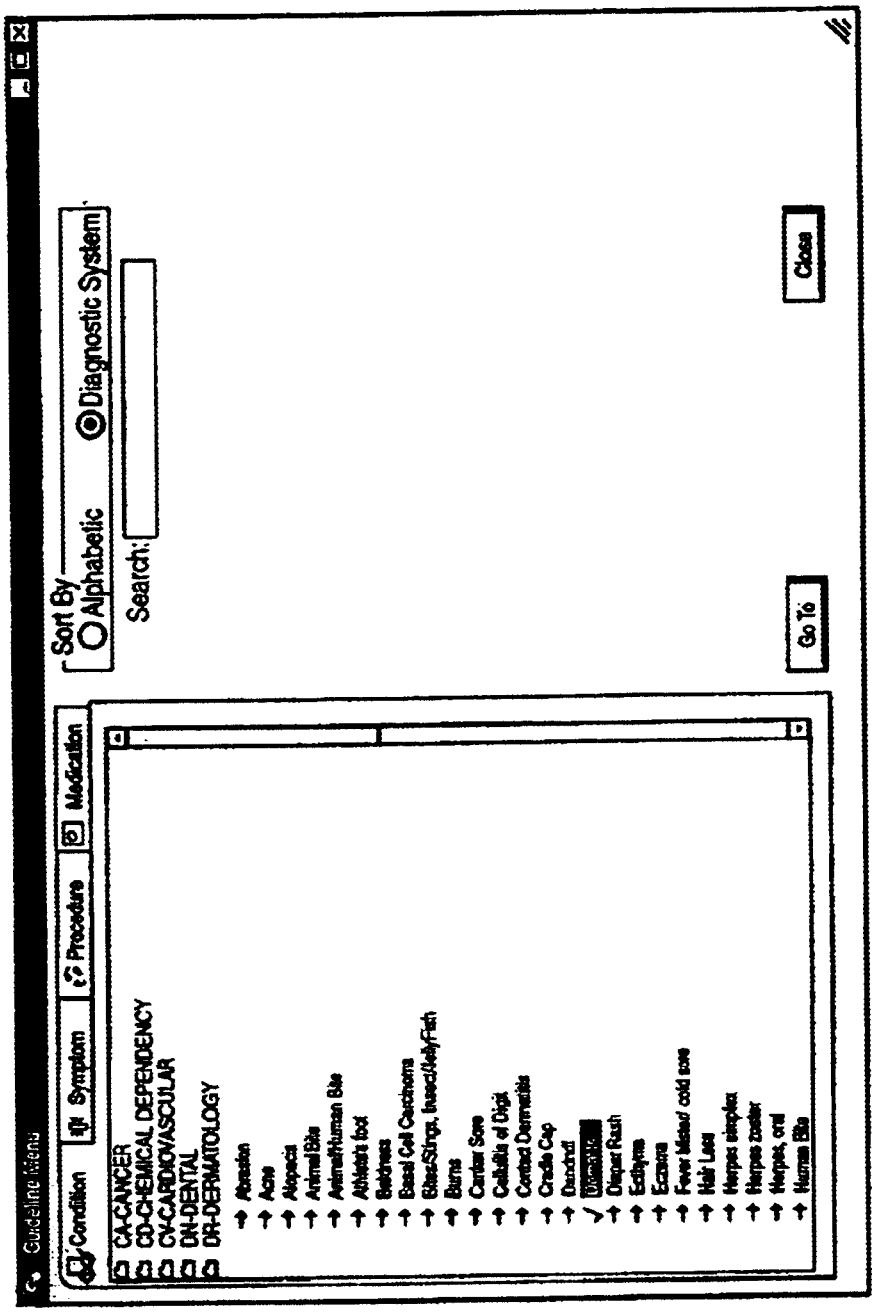
Figure 18:
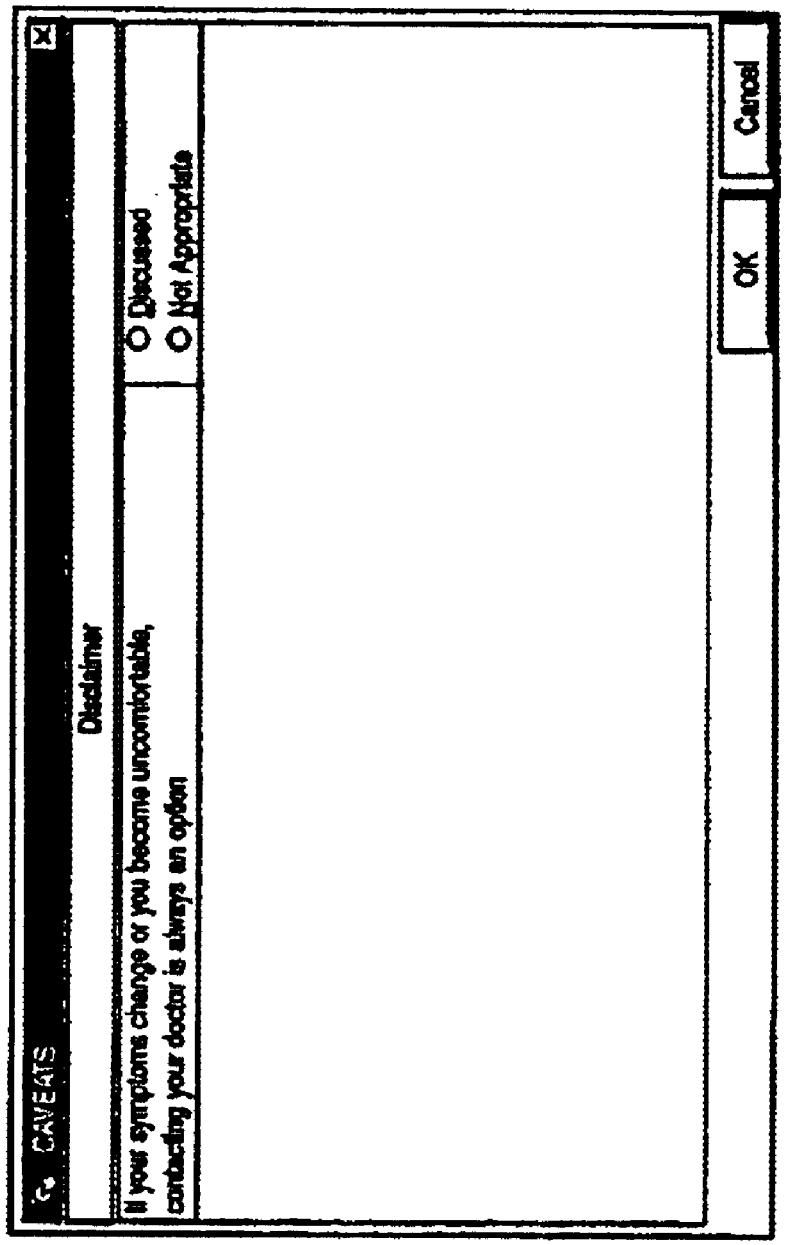
FIG. 18 illustrates an example screen or screen portion providing an operator with "caveats", or additional pieces of information upon which the operator may condition advice given to a caller.

For example, referring to FIG. 16, if a caller is complaining of a skin irritation, the caller may select a guideline relating to contact dermatitis 1601. The guideline may prompt the operator to ask the caller a series of questions 1602 relating to the caller's condition. The operator may enter the caller's responses to each question into the system's response input 1603, and the system may provide the operator with a disposition 1604 or suggested course of action to provide to the caller. An example of the screen from which an operator may select from various guidelines is illustrated in FIG. 17. The system may also provide the operator with one or more caveats, or additional pieces of information to provide to the caller, depending on the advice given. An example of such a "caveats" screen is illustrated in FIG. 18.

Figure 19:
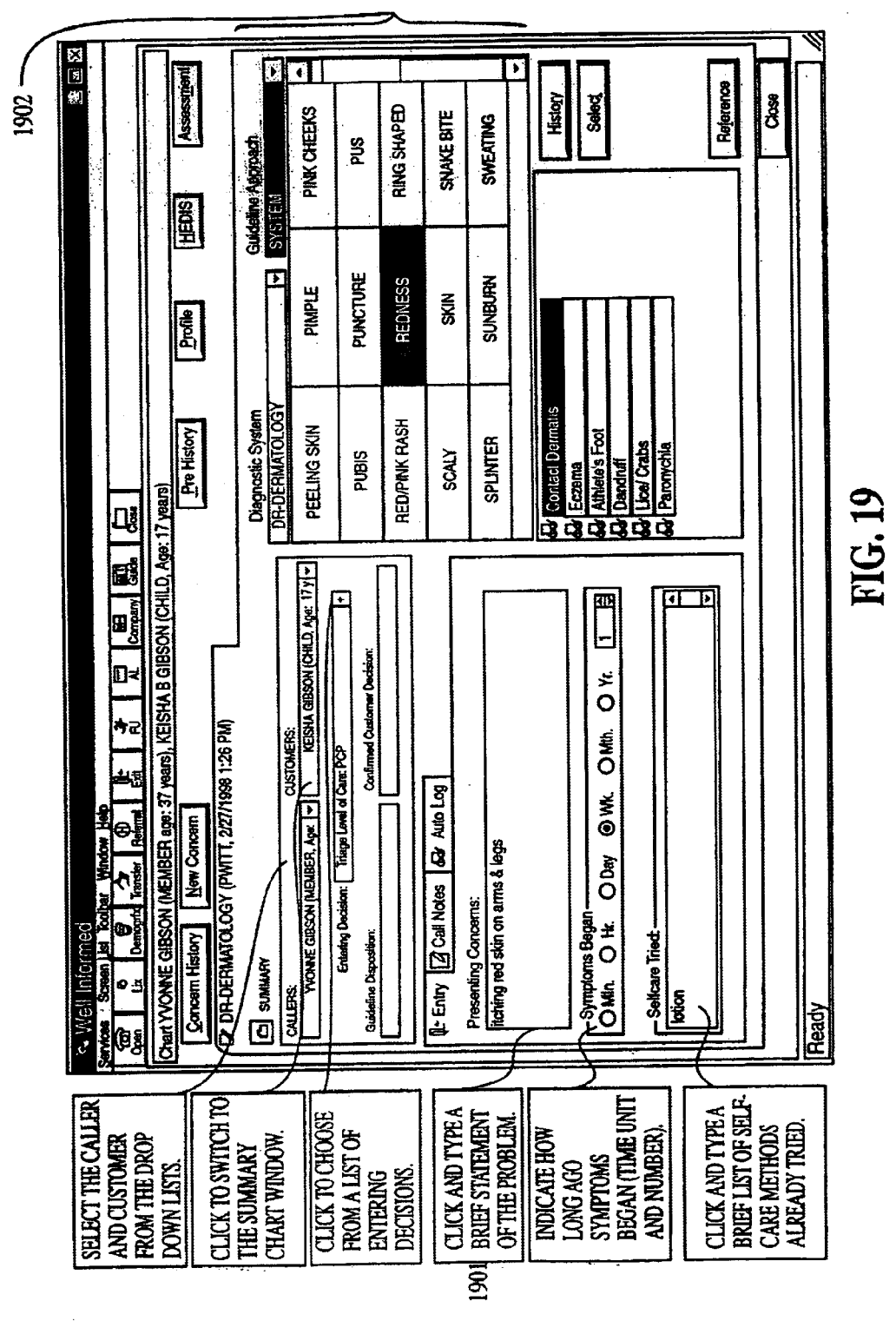

Referring back to FIG. 7, a unique feature and advantage of the system is its ability to automatically link the member profile information with rules, guidelines, and algorithms to help the operator provide advice and to generate alerts or messages 713 that are tailored to the individual needs of the caller. For example, when a caller is experiencing certain symptoms, the operator may enter those symptoms into the system via the client computer or network of computers. Referring to FIG. 19, the operator may enter this information via a dialogue box 1901 or by selecting from a group of pre-identified conditions 1902. The system will then compare the symptoms with the caller's prescription drug history and the information contained within the pharmaceutical information database to determine whether the symptoms may be a side effect of the caller's medication. Referring again to FIG. 7, the system may also automatically generate other types of outbound interventions 713 (i.e., alerts) such as prescription refill reminders, prescription renewal reminders, potential risks, and lists of the caller's allergies to medications, based on the caller's self-reported health information and recent contact history. The outbound interventions appear on the operator's display so that the operator can alert the caller about such items (e.g., prescription refills). Depending on the operator's level of authorization, the operator may optionally be permitted to directly request an original prescription or refill or renewal as described below or the operator may be able to transfer the caller to a different operator (such as a pharmacist) who has such authorization for such activities.

Figure 20:
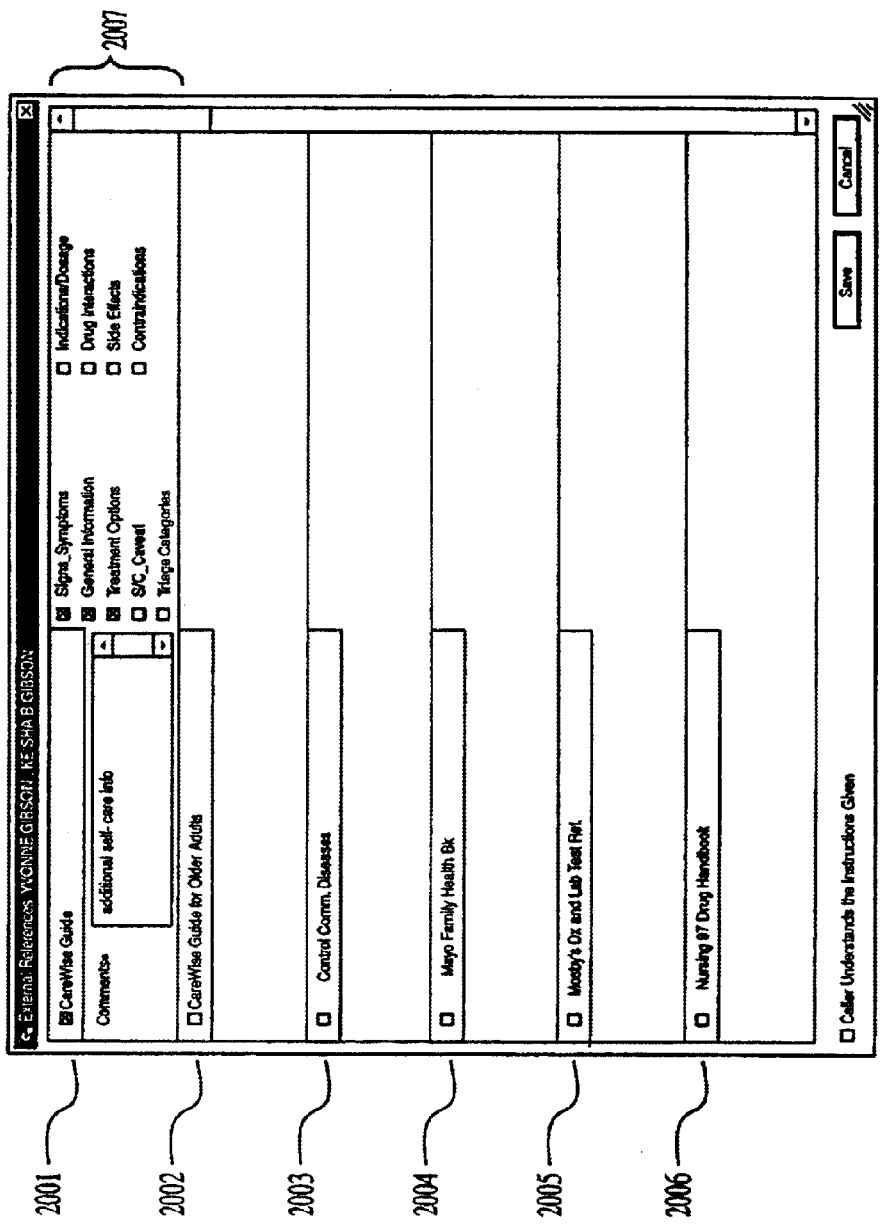
FIG. 20 illustrates an example of a screen whereby an operator may request that brochures, manuals or other materials be sent to a caller.

The system may also allow the operator to order written materials 714 or orders for future delivery to the caller, the caller's health care provider, or a pharmacist. For example, if the operator is a pharmacist, the operator may order a script which may be delivered to the caller, or to the caller's doctor, nurse, or pharmacy as described below. When generating a script, the operator may request, or the system may automatically provide, information relating to the drug prescribed from the pharmaceutical information database. A different operator may be able to generate or request clinical brochures or benefit manuals for delivery to the caller. As an additional example, referring to FIG. 20, an operator may select from various guide prompts 2001–2006 or prompts for portions of guides 2007.

Referring again to FIG. 7, if, while analyzing the caller's request and providing advice, the operator determines that the caller must visit a doctor, the operator may request that the system generate a referral 715 in accordance with health benefit plan rules and guidelines. The operator may, for example, access a database of participating providers and the rules associated with referring members to specific physicians, based on the symptom or condition described.

Figure 21A:
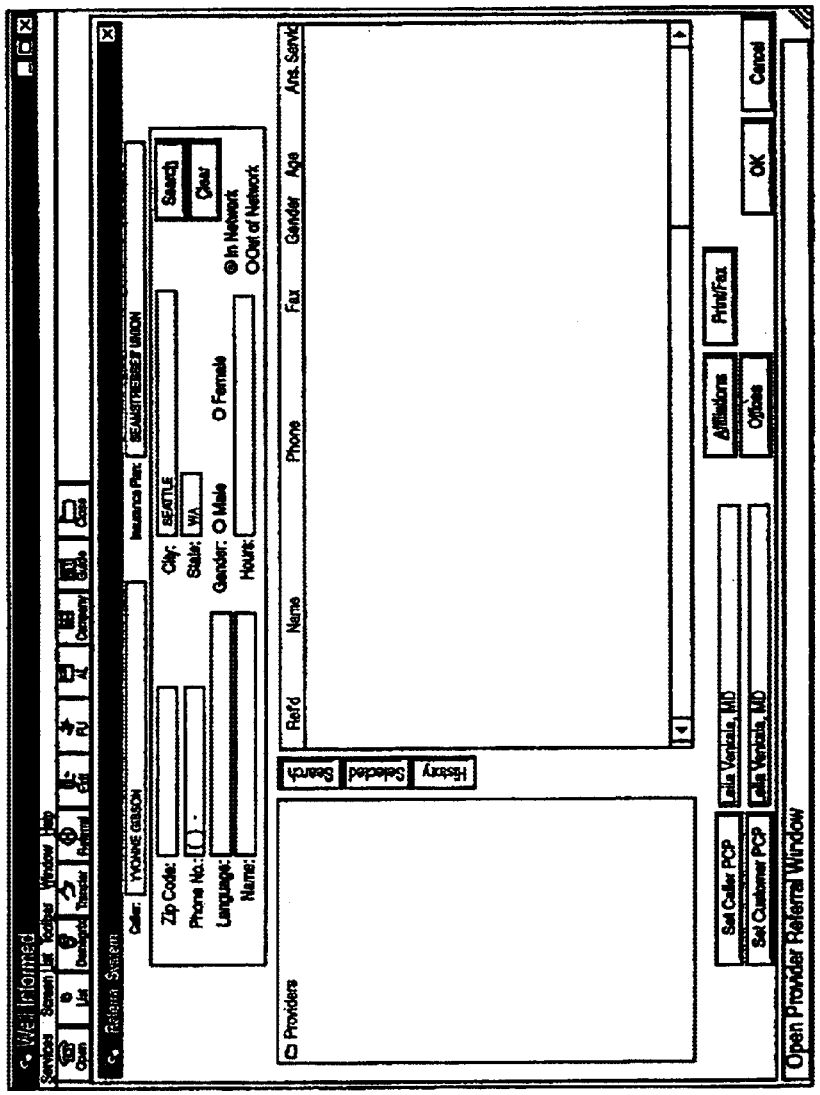
FIGS. 21a–21b illustrate an example screen whereby an operator may generate a referral by selecting from qualified providers.
Figure 21B:
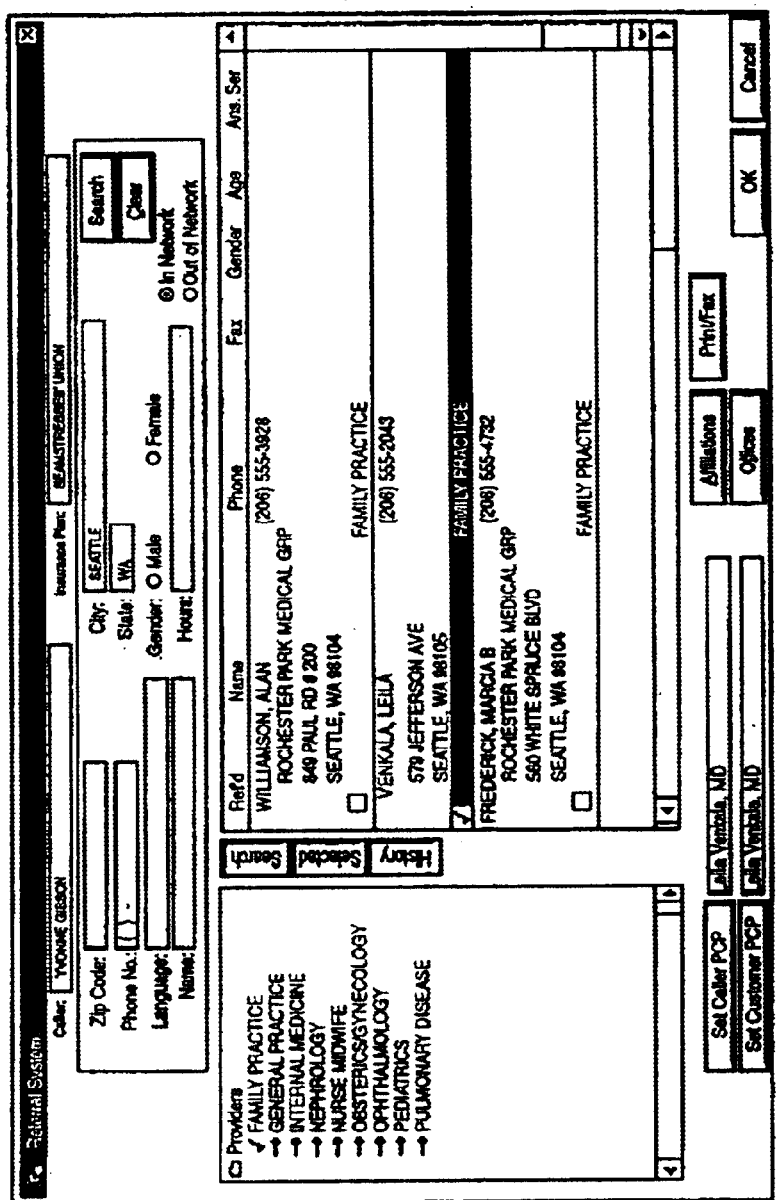

For example, referring to FIG. 21a, an operator may access a referral screen which prompts the operator to enter a geographic location and/or other information. FIG. 21b illustrates that the system may list several categories of providers 2101 as well as several possible providers within each category 2102. The system may also provide a database of general provider information, and it may support emergency room and other referrals based on client rules. The system may deliver notice of the referral directly to the health care provider as described below.

Figure 22:
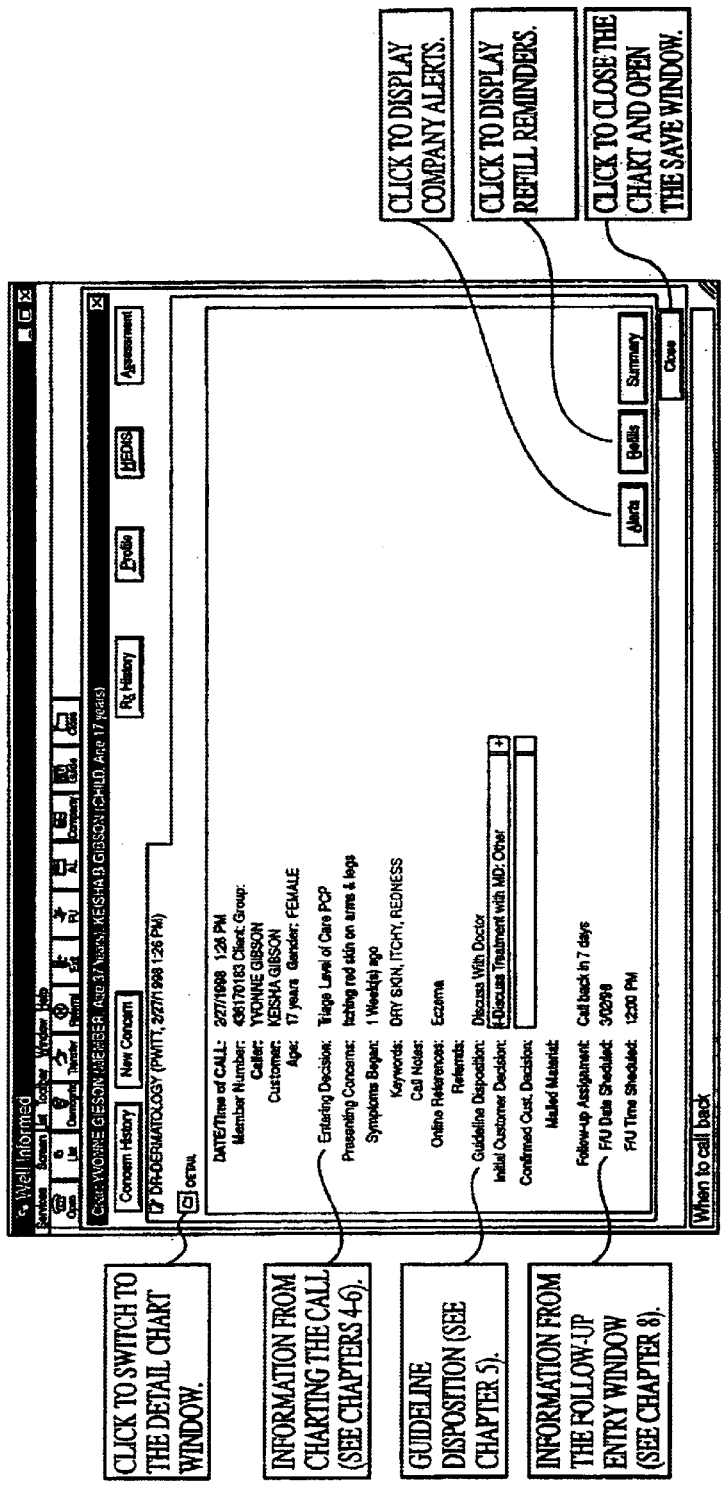
FIG. 22 illustrates an example of a member call summary screen.

During the course of and after the call, referring again to FIG. 7, the operator may update 716 the member profile (e.g., the caller's contact record) or create a new profile by entering information about the caller's inquiry and advice given, including information such as the caller's inquiry; any prescriptions ordered, refilled, or renewed; treatments suggested; and referrals provided. If the caller selected an audiotext topic, the system may automatically update the caller's record to identify the topics which the caller selected and the steps which the caller took to select the particular audiotext. As illustrated by FIG. 22, a call summary similar to a patient's handwritten chart may be generated using data that is automatically compiled based on the results of the call.

At the end of the call, referring again to FIG. 7, the system may notify 717 the caller's health care provider (such as a doctor or pharmacist) of the call. This provider notification 717 may include a package of information such as the caller's inquiry; any prescriptions ordered, refilled, or renewed; treatments or action items suggested; and referrals provided. The system may deliver this information automatically via facsimile, e-mail, or other delivery mechanism. Alternatively, the system may generate a call information report which the client may deliver to the provider via direct mail, telephone, or other manual delivery mechanism. The provider can then use this information when performing health care services on the caller's behalf. The provider may additionally or alternatively include the information in the provider's records for future reference.

Figure 23:
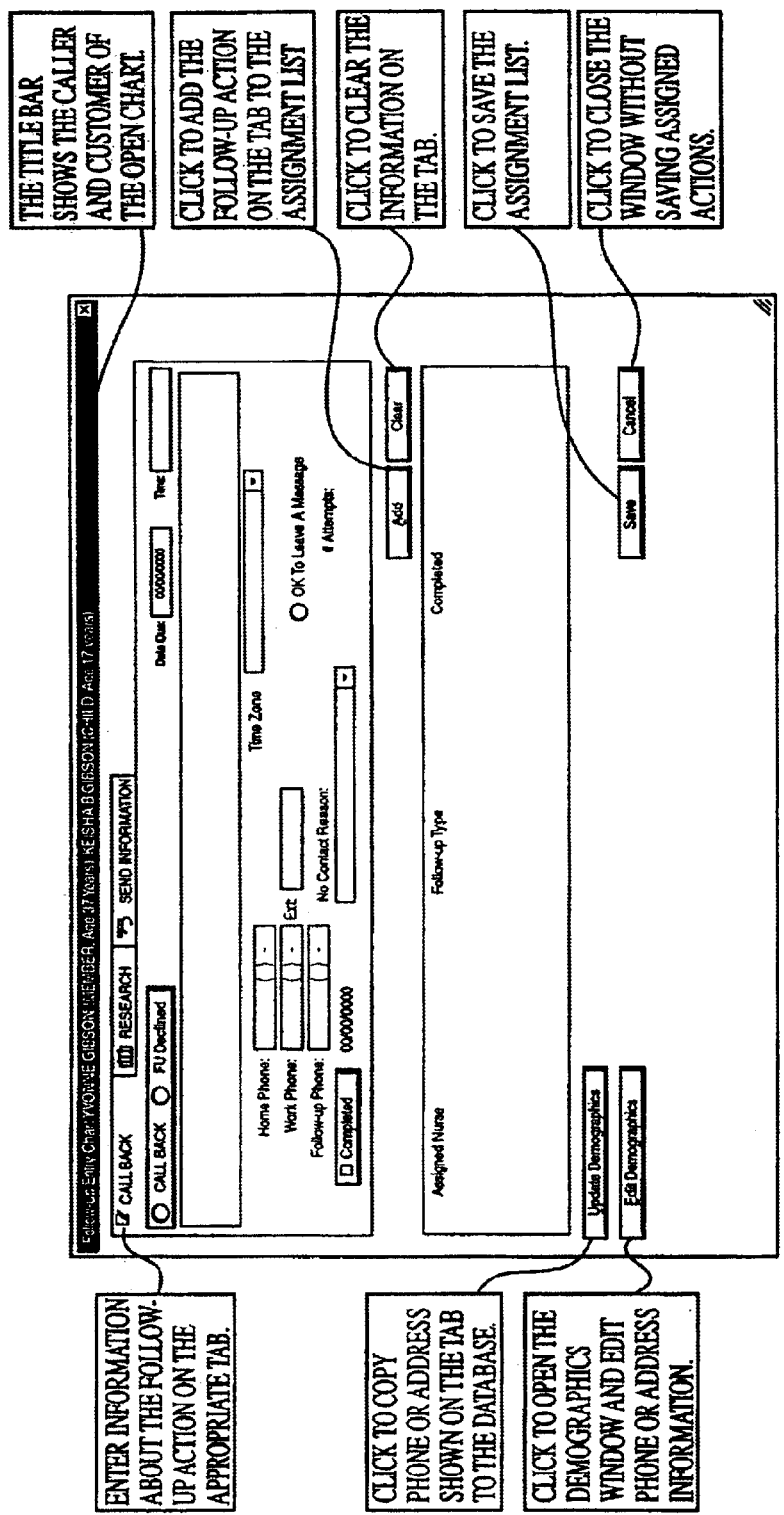
FIG. 23 illustrates an example of a screen whereby an operator may generate a follow-up report.

The system may also automatically generate or allow the operator to generate a report of follow-up actions that identifies tasks which the system, operator, provider, or other person or item must perform after completion of the call. FIG. 23 illustrates an example of a screen pursuant to which an operator may create a follow-up report. The follow-up actions may include tasks such as a reminder to call the member back after a certain period of time, a reminder to send the member certain information, or a reminder to perform research relating to the caller's request.

The system also prepares utilization reports 718 that are tailored to the specific needs of the client. For example, the system may monitor the time of each call or the number of times an individual caller contacts the system. The system may also monitor system usage volumes over time segments including quarter hour, half hour, hourly day part, daily, weekly, monthly, and year-to-date. The system may also generate reports that identify trends across a client's enrolled population.

Another feature of the reporting function 718 is that the system provides the ability to target members for follow up actions based on the information contained in the member profile database. If, for example, the client develops an informational pamphlet about a new drug or treatment that can benefit members who have experienced certain symptoms, the system can sort through the member profile database to identify members who have called with inquiries about such symptoms on recent calls. The system can also be used to identify members who could benefit from further use of the system, thus targeting such members for follow up with written or personally-provided (e.g., telephonic) information. The system can also automatically generate prescription refill reminders and prescription renewal reminders for an entire enrolled population or portion thereof so that the client can provide such reminders to the individual member via telephone, mail, or other delivery mechanism.

Additionally, the system includes a quality control function 719 to ensure that client-specified standards of performance are being met. The function may include features such as routine auditing of procedures and processes, random monitoring of a select number of calls, and a comparison of call reports with an overall set of performance standards.

III. Operating Features

Figure 8:
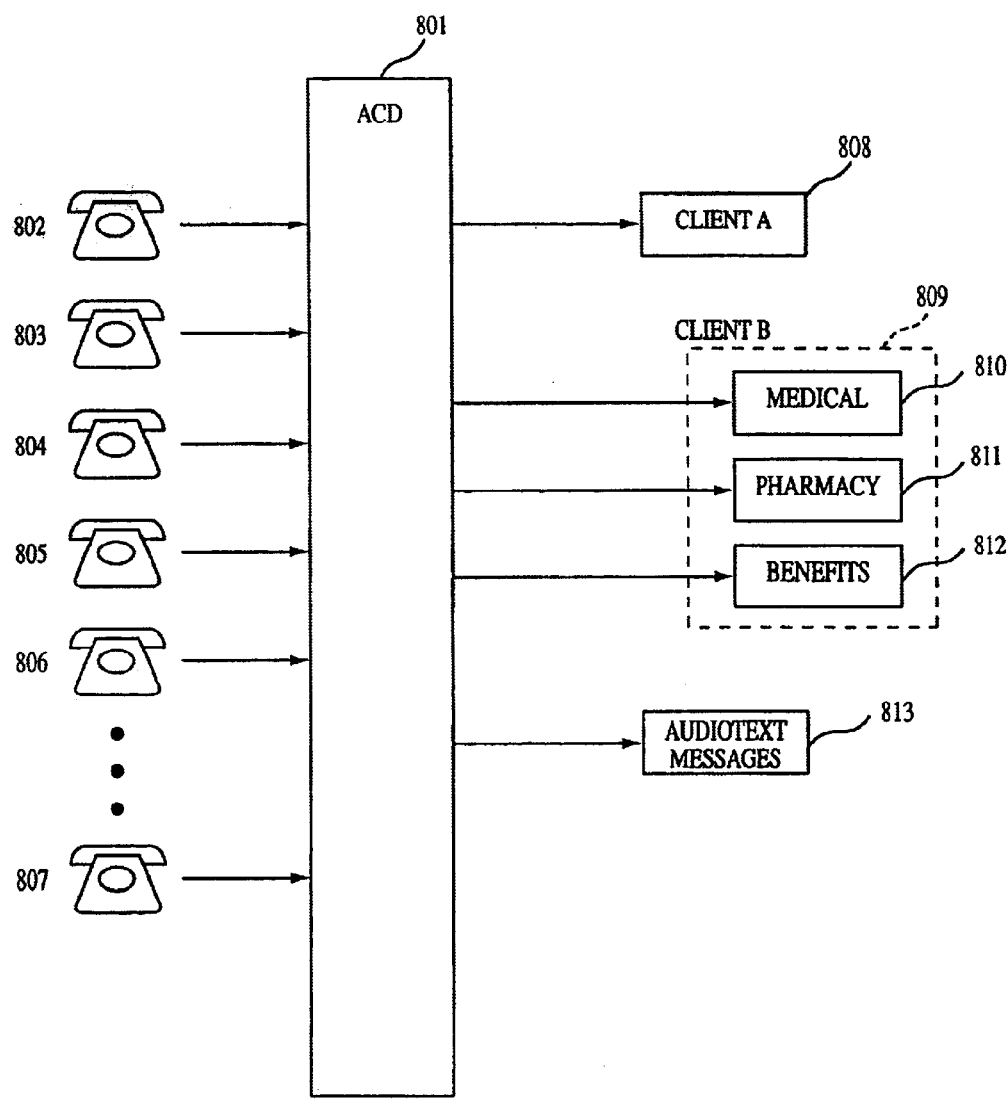
FIG. 8 is a diagram of the automated call distribution function defined in FIG. 7.

FIG. 8 is a detailed illustration of the automated call distribution feature identified on FIG. 7 as item 702. A plurality of telephone lines 802–807 are routed to the automated call distributor 801. The number of telephone lines illustrated on FIG. 8 is not fixed but rather illustrates one embodiment of the invention. Each telephone line has a unique access number, which is preferably but not required to be a toll-free number such as an 800 or 888 number. The automated call distributor 801 identifies the line number on which the incoming call arrives and routes the call based on that number. For example, the automated call distributor 801 may route all calls which arrive on telephone line 802 to client "A" 808. The automated call distributor may also route incoming calls to a particular operator of a particular client. For example, the automated call distributor may direct all calls that arrive on line 804 to the medical operator 810 of client "B" 809, while routing all calls arriving on line 805 to the client "B" pharmacy operator, and routing calls arriving on line 806 to the client "B" benefits operator 812.

The automated call distribution function may also serve as the service selection prompt function identified on FIG. 7 as item 703. For example, the automated call distributor 801 may recognize all calls arriving on line 802 as calls relating to client "B" 809. The automated call distributor 801 may then prompt each person who establishes communication on line 802 to select a particular operator for client "B" based on whether the caller's inquiry requires a medical operator, 810, a pharmacy operator 811, or a benefits operator 812. The automated call distributor 801 may also invite the caller to select a menu of audiotext messages 813.

Figure 9:
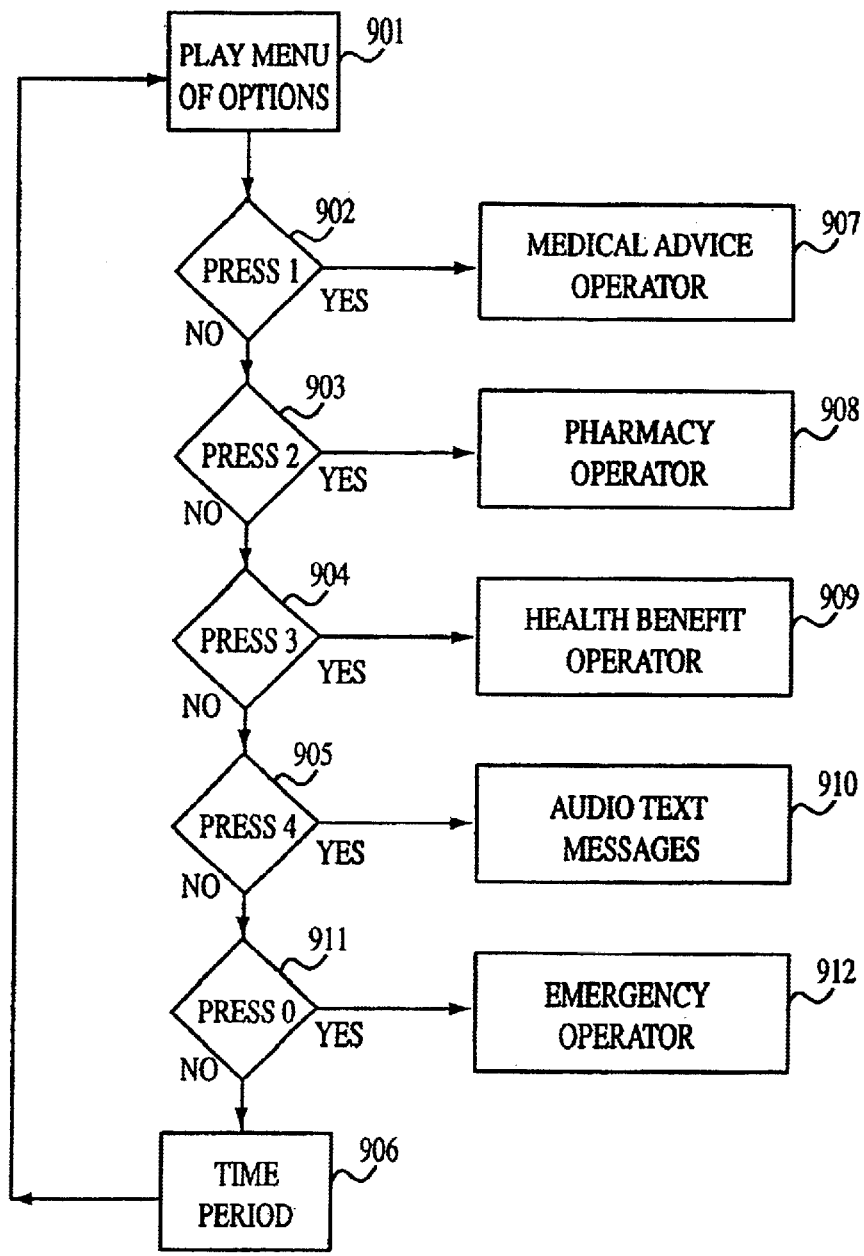
FIG. 9 is a diagram of the service selection prompt service selection processing, and operator connection functions defined in FIG. 7.

The service selection prompt function 703, service selection processing function 704, and operator connection function 705 of FIG. 7 are further illustrated on FIG. 9. These functions preferably begin by providing the caller with a menu of options 901. For example, the menu may invite the caller to press "1" 902 to speak with a medical operator 907 such as a nurse, nurse practitioner, or clinician; to press "2" 903 to speak with a pharmacy operator 908 such as a pharmacist or pharmacy assistant; to press "3" 904 to speak with a health benefit operator 909 such as an account representative or billing specialist; or to press "4" 905 to listen to pre-recorded audiotext messages 910 on a variety of subjects. If the caller does not make a selection within a specified time period 906, for example a ten second, twenty second, or thirty second period, the service selection prompt may replay the menu of options 901. The service selection prompt may provide additional options which invite the caller to press additional numbers to select specific services such as a prescription refill service, a referral service, etc. The service selection prompt may also be layered such that additional options are provided when a selection is made. For example, if the caller presses "2" 903 to select a pharmacy operator 908, the system may play a second menu which invites the caller to choose from a prescription refill specialist, an operator who can help with new prescriptions, or an operator who can provide specific prescription drug information. The service selection prompt may also provide for an emergency function which allows the caller to immediately speak with an operator who can assist the caller in the event of an emergency. For example, the caller may press "0" 911 to be immediately connected with an emergency operator 912.

Figure 10:
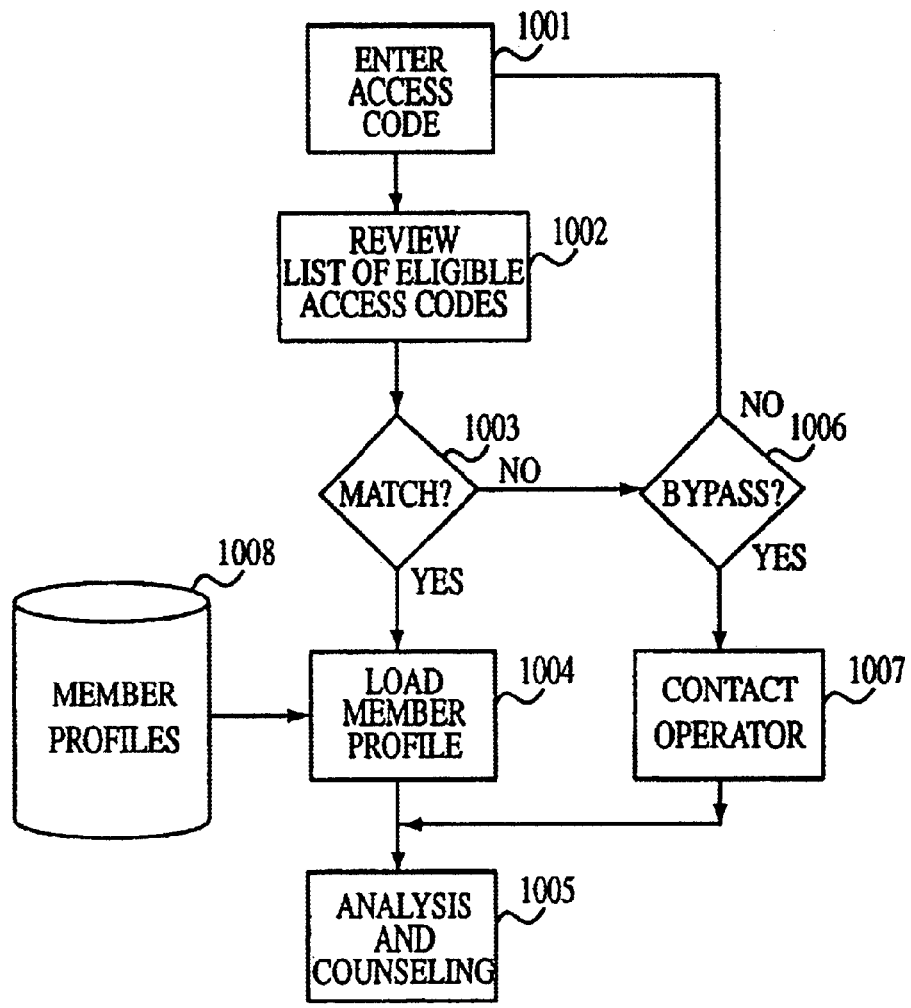
FIG. 10 is a diagram of the eligibility validation function defined in FIG. 7.

FIG. 10 illustrates the eligibility validation function identified as item 707 in FIG. 7. The eligibility validation function begins by inviting the caller to enter an access code 1001, which may consist of the caller's name, social security number, account number, or other unique form of identification. If the eligibility validation function occurs after the operator connection function is complete, the operator may enter the access code into the system at the operator's terminal on behalf of the caller. For example, the caller may provide the operator with the caller's name, or account number, and the operator may then input the name or account number into the system at the operator's computer terminal. Optionally, the eligibility validation function may be an automated function that is performed by the system prior to the operator connection function. For example, the automated call distributor may prompt the caller to enter the caller's account number via the touch tone pad on the caller's telephone, or the system may be equipped with a voice recognition device whereby the caller speaks the caller's name or account number into the telephone and the system thus obtains the caller's access code.

After the caller's access code is entered, the system reviews a list of eligible access codes 1002 and determines whether the caller's access code matches 1003 any of the eligible access codes. If the access code matches one of the eligible access codes, the system loads the member profile 1004 corresponding to the caller's access code from the member profile database 1008. The operator may then view the member profile to perform the analysis and counseling function 1005. If the caller's access code does not match any of the codes on the list of eligible access codes, the caller may again be prompted to re-enter its access code 1001, or the system may optionally be equipped with a by-pass function 1006 which allows the caller to speak with an operator 1007 for assistance in obtaining an access code to use the system. In lieu of a human operator, the system may optionally prompt the caller to dial a different number for assistance with obtaining an access code. In emergency situations, systems equipped with the by-pass function may allow the operator to initiate the analysis and counseling function 1005 without the benefit of the caller's member profile.

Figure 11:
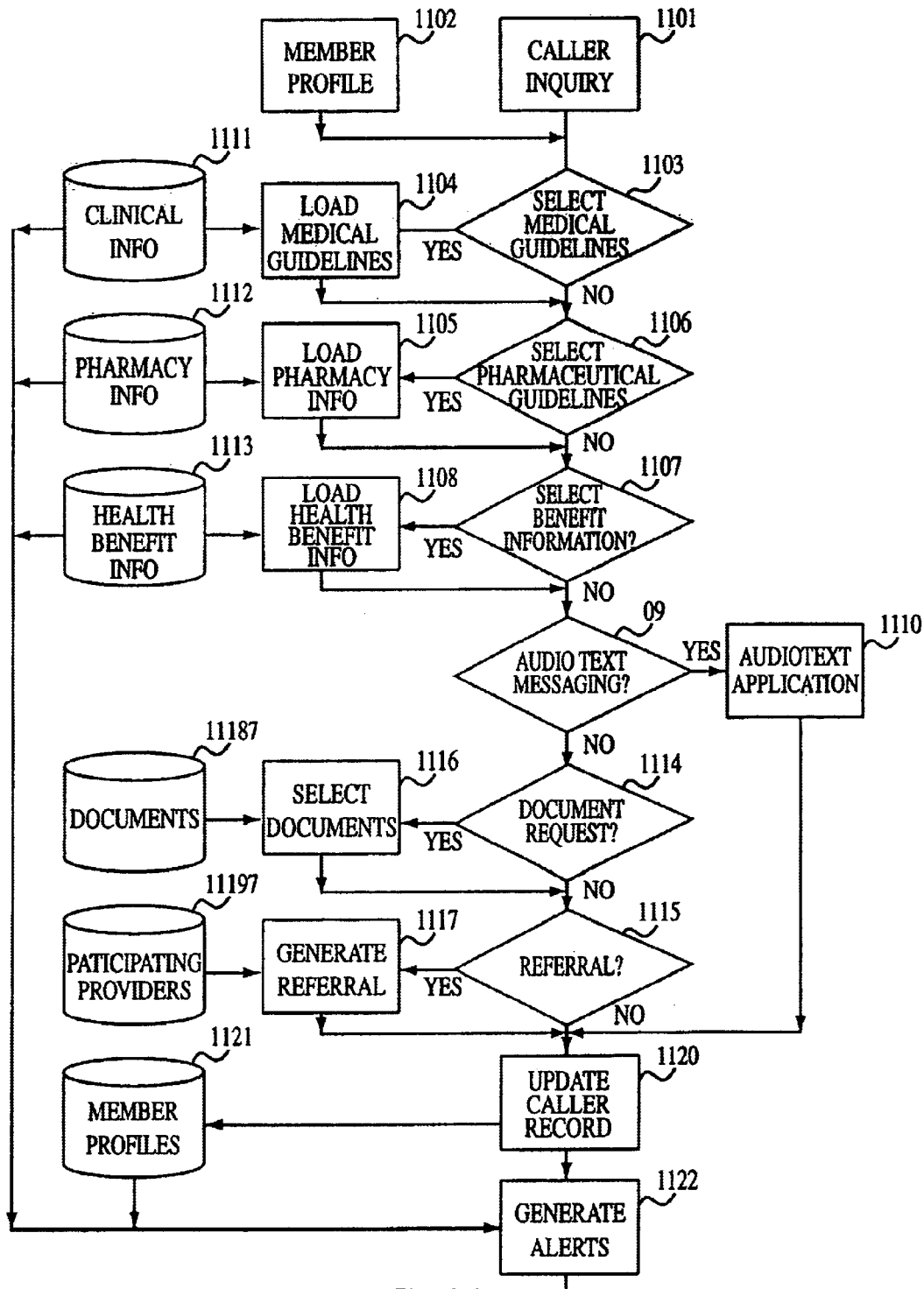
FIG. 11 is a diagram of the analysis and counseling, outbound interventions, document request, referral, and update caller record functions defined in FIG. 7.

FIG. 11 illustrates the analysis and counseling, outbound interventions, document request, referral, and update caller record functions identified on FIG. 7 as items 708, 713, 714, 715, and 716, respectively. After the member profile 1102 is loaded during the eligibility validation function, the operator asks the caller how the operator may provide assistance. The caller will explain the reason for the call 1101. If the caller is experiencing symptoms, complications, or is asking for assistance with an existing condition the operator will use the system's algorithms and guidelines to help determine the recommended course of action for the caller's particular situation. For example, if the caller is experiencing medical symptoms and requires clinical advice, the operator may direct the system to provide medical guidelines 1103, in which case the system will load medical guidelines 1104 from the clinical information database 1111. The operator may request that the system identify prescription drugs that can alleviate the caller's symptoms by choosing to the pharmaceutical guidelines 1106, in which case the system will load pharmaceutical information 1105 from the pharmaceutical information database 1112. If the caller's inquiry relates to account or benefits information rather than medical information, or if the operator requires information about the caller's available benefits to help provide advice to the caller, the operator may select benefits information 1107, in which the system loads health benefits information 1108 from the health benefits information database 1113. The operator's computer terminal is equipped with a screen or series or screens that detail and summarize the information loaded from the member profile database 1121, clinical information database 1111, pharmaceutical information database 1112, and health benefit information database 1113. This information will help the operator determine an appropriate course of action for the caller. For example, the clinical information database will include a plurality of medical guidelines, preferably at least 200 such guidelines, covering a plurality of, preferably at least 500, medical symptoms, conditions, procedures, and topics. The pharmaceutical information database 1112 and/or the clinical information database 1111 may also provide information about appropriate prescription and over-the-counter medications that will help alleviate particular symptoms.

The operator can also direct the system to route the caller to an audiotext application 1110 which contains pre-recorded messages on a number of, preferably at least 300, frequently used health care topics. The caller will be able to select a topic by a touch tone prompted menu, or the operator may select the topic for the caller. The caller can then be transferred to the audiotext message service or message menu for access to the audiotext message. The caller will have the opportunity to opt out of the audiotext facility and return to a live operator for further assistance or to terminate the phone call.

The operator may also request written documents 1114 for the caller. If the operator selects documents 1116, the operator will select from self-care texts, brochures, newsletters, promotional materials, and other written materials which may be automatically ordered from the system. The materials may be contained or identified in an optional documents database 1118. If the operator is authorized to do so, the operator may also direct the system to generate new prescriptions, prescription refills, or prescription renewals as part of the pharmacy request function. Depending on the nature of the advice provided to the caller, the operator may determine that a referral is necessary 1115, and generate a referral 1117 so that the caller may visit a participating provider. The system may optionally include a participating provider database 1119 to assist the operator in generating the referral.

During the course of the call and/or at the end of the call, the operator may update the member profile 1120 based on the inquiry made and advice given during the call. If the caller used the audiotext message service 1110, the system will automatically update the caller's member profile to indicate such usage. The operator may also ask the caller to provide an update of the caller's self-reported health information, such as data on allergies, existing health conditions, demographics that contribute to risk stratification, and other data applicable to helping the member with health care information needs. This information is stored in the member profile database 1121 during or at the end of the call.

During and/or at the end of the call, the system will also use the caller's member profile 1102, along with clinical information 1111, pharmaceutical information 1112, and health benefit information 1113 to generate alerts and messages for the operator to provide to the caller. These alerts and messages may relate to items such as appropriate prescription drug use, medications the caller should avoid or use in moderation or speak to a physician before using, suggested forms of treatment based on the caller's symptoms, prescription refill reminders, prescription renewal reminders, and other information. At the end of the call, the system may generate several types of reports and notices. For example, the system may have the capability to package information collected during the call, combined with specific pharmacy information, for delivery to the caller's physician, health plan, or other health care provider via facsimile, e-mail, direct mail, or other delivery mechanism. This information may include a summary of the items discussed during the call and the steps the caller has agreed with the operator to carry out. Such information may be used to assist the provider when performing health care services on the caller's behalf, or it may simply be used as reference information or become part of the caller's health information folder maintained by the provider. At the other end of the spectrum, the system may generate reports based on system usage to provide information such as number of calls per period of time, average length of call, referrals generated per call, and other information.

IV. Additional Information

The NCPDP Telecommunications Standard Format manual, including the standard format for the electronic submission of third party drug and/or medical claims, is hereby incorporated by reference. This report may be obtained from the National Council for Prescription Drug Programs, Inc., Phoenix, Ariz.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A computer-implemented and user assisted method of providing integrated decision support to gather, maintain and update medical, pharmaceutical, demographic, psychographic, and health benefit information of members and to maintain and provide medical, pharmaceutical, and customer service information and advice using a computer system, a caller, and one or more operators, said method comprising the steps of:

(a) receiving by the one or more operators a communication from the caller, the one or more operators receiving information in the communication from the caller explaining the reason for the communication including a health related issue associated with at least one pharmaceutical that the caller is currently using;

(b) providing, by the computer system, the one or more operators with member profile information associated with the caller including health benefit plan information, prescription drug history, self-reported health information, and recent contact history, including, when present, a list of allergies, prescriptions, and pre-existing health conditions associated with the caller;

(c) providing, by the computer system, the one or more operators access to at least one database storing clinical information including clinical guidelines, clinical rules, clinical algorithms, clinical operating protocols, and clinical procedures to assist the one or more operators in identifying recommended forms of treatment, medications, and courses of action for the caller responsive to the communication;

(d) providing, prior to diagnosis by a physician with respect to the communication from the caller and the health related issue relating thereto, by the computer system, the one or more operators with pharmaceutical information including prescription drug side effects and complications that may be associated with particular drugs or combinations of drugs that the caller is currently using or which the one or more over-the-counter medications operators intend to recommend, and health benefit information including insurance company rules, member information, and benefit plan resources associated with the pharmaceutical information;

(e) automatically linking, prior to the diagnosis by the physician, by the computer system, the member profile information including the health benefit plan information, the prescription drug history, the self-reported health information, and the recent contact history, with the pharmaceutical information and the clinical rules, the clinical guidelines, and the clinical algorithms to assist the one or more operators in providing advice for the communication;

(f) generating, prior to the diagnosis by the physician, by the computer system, responsive to said providing steps (b), (c) and (d) and linking step (e) at least one of alerts and messages that are designed for the communication by caller, the messages including appropriate prescription drug use, medications the caller should avoid or use in moderation or speak to a physician before using, suggested forms of treatment based on the caller's symptoms, prescription refill reminders, and prescription renewal reminders;

(g) generating, by the computer system, at least one of reports with respect to the health related issue and notices including information collected during the communication with the caller, combined with specific pharmacy information, for delivery to the physician of the caller, and the caller's health plan with respect to the health related issue;

(h) receiving by at least one of the physician of the caller and the caller's health plan the at least one of reports and notices to assist performing health care services by the one of the physician or the caller's health plan;

(i) targeting for follow up action, by the computer system, members of the health plan using the member profile information including the health benefit plan information, the prescription drug history, the self-reported health information, and the recent contact history in combination with the messages including the appropriate prescription drug use, the suggested forms of treatment based on the caller's symptoms, the prescription refill reminders, and the prescription renewal reminders; and (j) targeting for new action, by the computer system, the members associated with the health plan using the member profile information including the health benefit plan information, the prescription drug history, the self-reported health information, and the recent contact history when at least one of the clinical information, the pharmaceutical information and the health benefit information are updated.

2. A computer-implemented and user assisted method of providing integrated decision support according to claim 1, further comprising the steps of ensuring that client-specified standards of performance are being met, including auditing of procedures and processes, random monitoring of a select number of calls, and a comparison of call reports with an overall set of performance standards.

3. A computer-implemented and user assisted method of providing integrated decision support according to claim 2, further comprising the steps of requesting by the one or more operators, using the computer system, written documents for the caller including self-care texts, brochures, newsletters, promotional materials, and other written materials which may be automatically ordered from the computer system for current and future delivery to the caller, the caller's health care plan, a physician, and optionally a pharmacist.

4. A computer-implemented and user assisted method of providing integrated decision support according to claim 3, further comprising the steps of requesting by the one or more operators, using the computer system, at least one of a new prescription, a prescription refill and a prescription renewal and arranging for direct delivery to or pick up by the caller.

5. A computer-implemented and user assisted method of providing integrated decision support according to claim 4, further comprising the steps of determining by the one or more operators, using the computer system, while analyzing the communication from the caller, that the caller must visit a physician, requesting that the computer system generate a referral in accordance with the health benefit plan rules, and accessing a database of participating providers and rules associated with referring members to specific physicians, based on the health related issue described by the caller.

6. A computer-implemented and user assisted method of providing integrated decision support according to claim 5, further comprising the steps of generating a report including the caller's communication, any prescriptions ordered, refilled, or renewed, treatments or action items suggested, and referrals provided to the caller using the computer system, and notifying the health care plan associated with the caller and a health care provider associated with the caller for updating and follow up action or treatment.

7. A computer-implemented and user assisted method of providing integrated decision support according to claim 6, further comprising the steps of updating by the one or more operators, using the computer system, while analyzing the communication from the caller, the member profile based on the communication and information given by the caller, and updating by the one or more operators the caller's self-reported health information that includes data on the allergies, existing health conditions, demographics that contribute to risk stratification, and other data applicable to helping the member with health care information needs.

8. A computer-implemented and user assisted method of providing integrated decision support according to claim 1, further comprising the steps of ensuring that client-specified standards of performance are being met, including auditing of procedures and processes, random monitoring of a select number of calls, and a comparison of call reports with an overall set of performance standards.

9. A computer-implemented and user assisted method of providing integrated decision support according to claim 1, further comprising the steps of requesting by the one or more operators using the computer system, written documents for the caller including self-care texts, brochures, newsletters, promotional materials, and other written materials which may be automatically ordered from the computer system for current and future delivery to the caller, the caller's health care plan, a physician, and optionally a pharmacist.

10. A computer-implemented and user assisted method of providing integrated decision support according to claim 1, further comprising the steps of requesting by the one or more operators, using the computer system, at least one of a new prescription, a prescription refill and a prescription renewal and arranging for direct delivery to or pick up by the caller.

11. A computer-implemented and user assisted method of providing integrated decision support according to claim 1, further comprising the steps of determining by the one or more operators, using the computer system, while analyzing the communication from the caller, that the caller must visit a physician, requesting that the computer system generate a referral in accordance with the health benefit plan rules, and accessing a database of participating providers and rules associated with referring members to specific physicians, based on the health related issue described by the caller.

12. A computer-implemented and user assisted method of providing integrated decision support according to claim 1, further comprising the steps of generating a report including the caller's communication, any prescriptions ordered, refilled, or renewed, treatments or action items suggested, and referrals provided to the caller using the computer system, and notifying the health care plan associated with the caller and a health care provider associated with the caller for updating and follow up action or treatment.

13. A computer-implemented and user assisted method of providing integrated decision support according to claim 1, further comprising the steps of updating by the one or more operators, using the computer system, while analyzing the communication from the caller, the member profile based on the communication and information given by the caller, and updating by the one or more operators the caller's self-reported health information that includes data on the allergies, existing health conditions, demographics that contribute to risk stratification, and other data applicable to helping the member with health care information needs.

14. A computer-assisted method of providing clinical, pharmaceutical, and health benefit information and advice according to claim 1, further comprising the step of updating a member record in the member information database to include the one or more of clinical advice, pharmaceutical advice, and health benefit advice provided to the caller.

15. A computer-assisted method of providing clinical, pharmaceutical, and health benefit information and advice according to claim 1, further comprising the step of notifying a health care provider of the one or more of clinical advice, pharmaceutical advice, and health benefit advice.

16. A computer system of providing integrated decision support to gather, maintain and update medical, pharmaceutical, demographic, psychographic, and health benefit information of members and to maintain and provide medical, pharmaceutical, and customer service information and advice using a computer system, a caller, and one or more operators, comprising:
  (a) means for receiving by the one or more operators a communication from the caller, the one or more operators receiving information in the communication from the caller explaining the reason for the communication including a health related issue associated with at least one pharmaceutical that the caller is currently using;
  (b) means for providing, by the computer system, the one or more operators with member profile information associated with the caller including health benefit plan information, prescription drug history, self-reported health information, and recent contact history, including, when present, a list of allergies, prescriptions, and pre-existing health conditions associated with the caller;
  (c) means for providing, by the computer system, the one or more operators access to at least one database storing clinical information including clinical guidelines, clinical rules, clinical algorithms, clinical operating protocols, and clinical procedures to assist the one or more operators in identifying recommended forms of treatment, medications, and courses of action for the caller responsive to the communication;
  (d) means for providing, prior to diagnosis by a physician with respect to the communication from the caller and the health related issue relating thereto, by the computer system, the one or more operators with pharmaceutical information including prescription drug side effects and complications that may be associated with particular drugs or combinations of drugs that the caller is currently using or which the one or more operators intends to recommend, and health benefit information including insurance company rules, member information, and benefit plan resources associated with the pharmaceutical information;
  (e) means for automatically linking, prior to the diagnosis by the physician, by the computer system, the member profile information including the health benefit plan information, the prescription drug history, the self-reported health information, and the recent contact history, with the pharmaceutical information and the clinical rules, the clinical guidelines, and the clinical algorithms to assist the one or more operators in providing advice for the communication;
  (f) means for generating, by the computer system, prior to the diagnosis by the physician, at least one of alerts and messages that are designed for the communication by the caller, the messages including appropriate prescription drug use, medications the caller should avoid or use in moderation or speak to a physician before using, suggested forms of treatment based on the caller's symptoms, prescription refill reminders, and prescription renewal reminders;
  (g) means for generating, by the computer system, at least one of with respect to the health related issue reports and notices including information collected during the communication with the caller, combined with specific pharmacy information, for delivery to the physician of the caller, and the caller's health plan with respect to the health related issue;
  (h) means for receiving by at least one of the physician of the caller and the caller's health plan the at least one of reports and notices to assist performing health care services by the one of the physician or the caller's health plan;
  (i) means for targeting for follow up action, by the computer system, members of the health plan using the member profile information including the health benefit plan information, the prescription drug history, the self-reported health information, and the recent contact history in combination with the messages including the appropriate prescription drug use, the suggested forms of treatment based on the caller's symptoms, the prescription refill reminders, and the prescription renewal reminders; and
  (j) means for targeting for new action, by the computer system, the members associated with the health plan using the member profile information including the health benefit plan information, the prescription drug history, the self-reported health information, and the recent contact history when at least one of the clinical information, the pharmaceutical information and the health benefit information are updated.

17. A computer-implemented and user assisted method of providing integrated decision support to gather, maintain and update medical, pharmaceutical, demographic, psychographic, and health benefit information of members and to maintain and provide medical, pharmaceutical, and customer service information and advice using a computer system, a caller, and one or more operators, said method comprising the steps of:
  (a) receiving by the one or more operators a communication from the caller, the one or more operators receiving information in the communication from the caller explaining the reason for the communication including a health related issue associated with at least one pharmaceutical that the caller is currently using;

(b) providing, by the computer system, the one or more operators with member profile information associated with the caller including health benefit plan information, prescription drug history, self-reported health information, and recent contact history, including, when present, a list of allergies, prescriptions, and pre-existing health conditions associated with the caller;

(c) providing, by the computer system, the one or more operators access to at least one database storing clinical information including clinical guidelines, clinical rules, clinical algorithms, clinical operating protocols, and clinical procedures to assist the one or more operators in identifying recommended forms of treatment, medications, and courses of action for the caller responsive to the communication;

(d) providing, prior to diagnosis by a physician with respect to the communication from the caller and the health related issue relating thereto, by the computer system, the one or more operators with pharmaceutical information including prescription drug side effects and complications that may be associated with particular drugs or combinations of drugs that the caller is currently using or which the one or more operators intends to recommend, and health benefit information including insurance company rules, member information, and benefit plan resources associated with the pharmaceutical information;

(e) automatically linking, prior to the diagnosis by the physician, by the computer system, the member profile information including the health benefit plan information, the prescription drug history, the self-reported health information, and the recent contact history, with the pharmaceutical information and the clinical rules, the clinical guidelines, and the clinical algorithms to assist the one or more operators in providing advice for the communication;

(f) generating, prior to the diagnosis by the physician, by the computer system, responsive to said providing steps (b), (c) and (d) and linking step (e) at least one of alerts and messages that are designed for the caller, the messages including appropriate prescription drug use, medications the caller should avoid or use in moderation or speak to a physician before using, suggested forms of treatment based on the caller's symptoms, prescription refill reminders, and prescription renewal reminders;

(g) generating, by the computer, system, at least one of with respect to the health related issue reports and notices including information collected during the communication with the caller, combined with specific pharmacy information, for delivery to the physician of the caller, and the caller's health plan with respect to the health related issue;

(h) receiving by at least one of the physician of the caller and the caller's health plan the at least one of reports and notices to assist performing health care services by the one of the physician or the caller's health plan;

(i) targeting for follow up action, by the computer system, members of the health plan using the member profile information including the health benefit plan information, the prescription drug history, the self-reported health information, and the recent contact history in combination with the messages including the appropriate prescription drug use, the suggested forms of treatment based on the caller's symptoms, the prescription refill reminders, and the prescription renewal reminders;

(j) targeting for new action, by the computer system, the members associated with the health plan using the member profile information including the health benefit plan information, the prescription drug history, the self-reported health information, and the recent contact history when at least one of the clinical information, the pharmaceutical information and the health benefit information are updated;.

(k) ensuring that client-specified standards of performance are being met, including auditing of procedures and processes, random monitoring of a select number of calls, and a comparison of call reports with an overall set of performance standards;

(l) requesting by the one or more operators, using the computer system, written documents for the caller including self-care texts, brochures, newsletters, promotional materials, and other written materials which may be automatically ordered from the computer, system for current and future delivery to the,caller, the caller's health care plan, a physician, and optionally a pharmacist;

(m) requesting by the one or more operators, using the computer system, at least one of a new prescription, a prescription refill and a prescription renewal and arranging for direct delivery to or pick up by the caller;

(n) determining by the one or more operators, using the computer system, while analyzing the communication from the caller, that the caller must visit a physician, requesting that the computer system generate a referral in accordance with the health benefit plan rules, and accessing a database of participating providers and rules associated with referring members to specific physicians, based on the health related issue described by the caller;

(o) generating a report including the caller's communication, any prescriptions ordered, refilled, or renewed, treatments or action items suggested, and referrals provided to the caller using the computer system, and notifying the health care plan associated with the caller and a health care provider associated with the caller for updating and follow up action or treatment;

(p) updating by the one or more operators, using the computer system, while analyzing the communication from the caller, the member profile based on the communication and information given by the caller, and updating by the one or more operators the caller's self-reported health information that includes data on the allergies, existing health conditions, demographics that contribute to risk stratification, and other data applicable to helping the member with health care information needs;

(q) updating a member record in the member information database to include the one or more of clinical advice, pharmaceutical advice, and health benefit advice provided to the caller; and (r) notifying a health care provider of the one or more of clinical advice, pharmaceutical advice, and health benefit advice.

* * * * *